US007285787B2

United States Patent
Horigome et al.

(10) Patent No.: US 7,285,787 B2
(45) Date of Patent: Oct. 23, 2007

(54) EPI-ILLUMINATION MICROSCOPE AND FLUORESCENCE FILTER SET

(75) Inventors: Shuhei Horigome, Ina (JP); Tadashi Watanabe, Kamiina-gun (JP)

(73) Assignee: Olympus Corporation, Shibuya-ku, Tokyo (JP)

( * ) Notice: Subject to any disclaimer, the term of this patent is extended or adjusted under 35 U.S.C. 154(b) by 318 days.

(21) Appl. No.: 11/097,351

(22) Filed: Apr. 4, 2005

(65) Prior Publication Data

US 2005/0231715 A1 Oct. 20, 2005

(30) Foreign Application Priority Data

Apr. 5, 2004 (JP) ............................. 2004-111356
Dec. 8, 2004 (JP) ............................. 2004-355747

(51) Int. Cl.
*G01K 1/08* (2006.01)
*G01J 3/30* (2006.01)

(52) U.S. Cl. ...................................... 250/400; 356/317

(58) Field of Classification Search ................ 250/400, 250/458.1, 461.1, 398, 459.1; 359/368, 389, 359/584, 585, 586, 587, 588, 589, 629, 839; 356/317

See application file for complete search history.

(56) References Cited

U.S. PATENT DOCUMENTS

| | | | |
|---|---|---|---|
| 3,853,386 A * | 12/1974 | Ritter et al. ................. 359/588 |
| 3,973,827 A * | 8/1976 | Uetake ........................ 359/355 |
| 4,806,750 A * | 2/1989 | Vincent ....................... 250/226 |
| 5,072,382 A * | 12/1991 | Kamentsky .................. 382/133 |
| 5,339,198 A * | 8/1994 | Wheatly et al. ............. 359/359 |
| 5,341,238 A * | 8/1994 | Trost et al. .................. 359/359 |
| 5,371,624 A * | 12/1994 | Nagano et al. .............. 359/389 |
| 5,710,663 A * | 1/1998 | Kawasaki .................... 359/389 |
| 6,262,837 B1* | 7/2001 | Nagano et al. .............. 359/368 |
| 6,633,375 B1* | 10/2003 | Veith et al. ............... 356/237.4 |
| 6,747,280 B1* | 6/2004 | Weiss ....................... 250/458.1 |
| 6,750,457 B2* | 6/2004 | Heffelfinger et al. ..... 250/458.1 |
| 6,906,859 B2* | 6/2005 | Nihoshi et al. .............. 359/389 |
| 2003/0044967 A1* | 3/2003 | Heffelfinger et al. .... 435/287.2 |
| 2005/0179899 A1* | 8/2005 | Palti-Wasserman et al. 356/417 |
| 2006/0028729 A1* | 2/2006 | Nishiwaki et al. .......... 359/580 |
| 2006/0192081 A1* | 8/2006 | Cartlidge et al. ........ 250/208.1 |

* cited by examiner

*Primary Examiner*—David Porta
*Assistant Examiner*—Faye Boosalis
(74) *Attorney, Agent, or Firm*—Kenyon & Kenyon LLP

(57) ABSTRACT

A microscope has a light source that emits light to illuminate a sample, a first wavelength selection member that selectively transmits the light from the light source, a light splitter that reflects the light from the first wavelength selection member to epi-illuminate the sample and transmits the light emitted from the sample, and a second wavelength selection member that selectively transmits the light transmitted through the light splitter. The light splitter is constituted of a transparent member and a dichroic mirror coat disposed on the transparent member. The dichroic mirror coat is constituted of a stacked layer that efficiently reflects light having a wavelength selected by the first wavelength selection member and a stacked layer that reflects light on a short wavelength side from the light selected by the first wavelength selection member, light on a long wavelength side, light of the same band, or combined light.

28 Claims, 9 Drawing Sheets

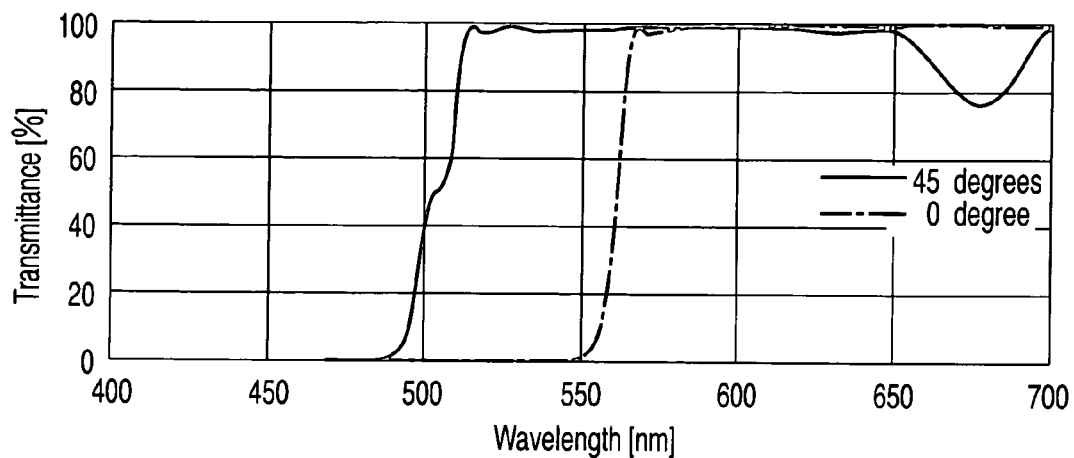
F I G. 12
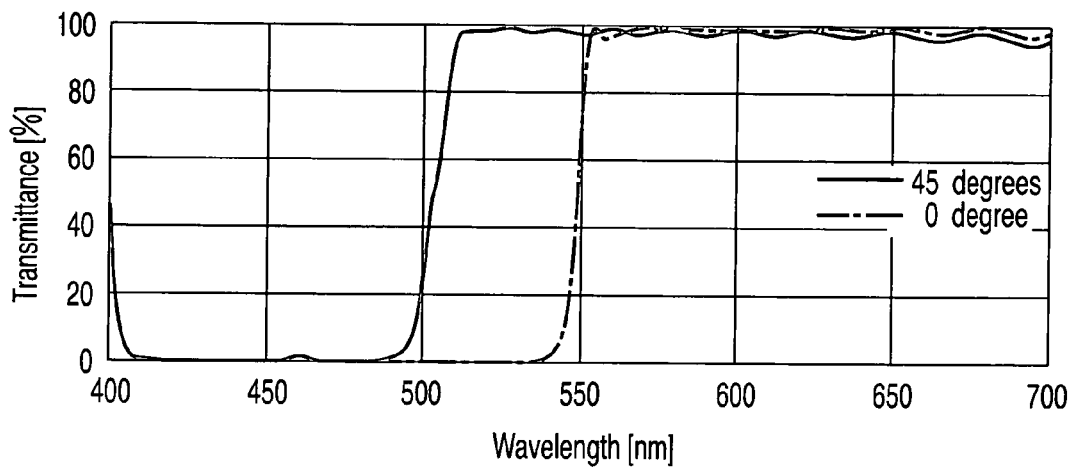
F I G. 13
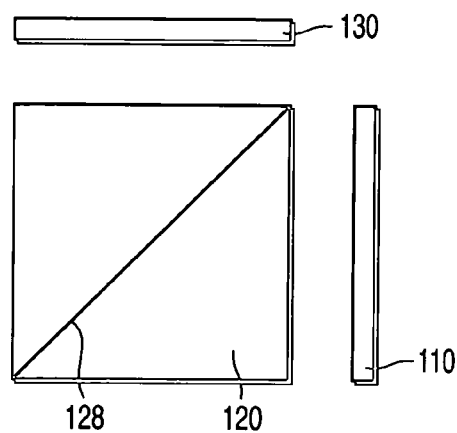
F I G. 14

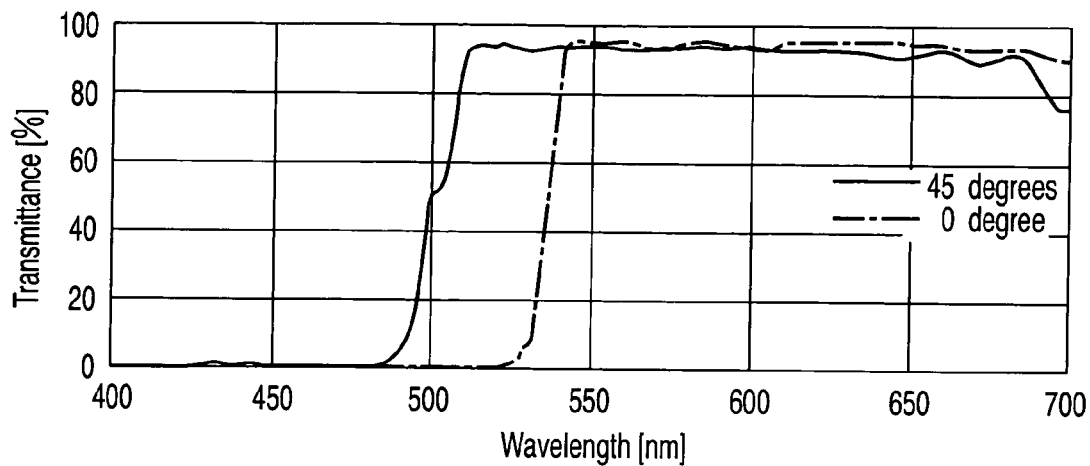
F I G. 15
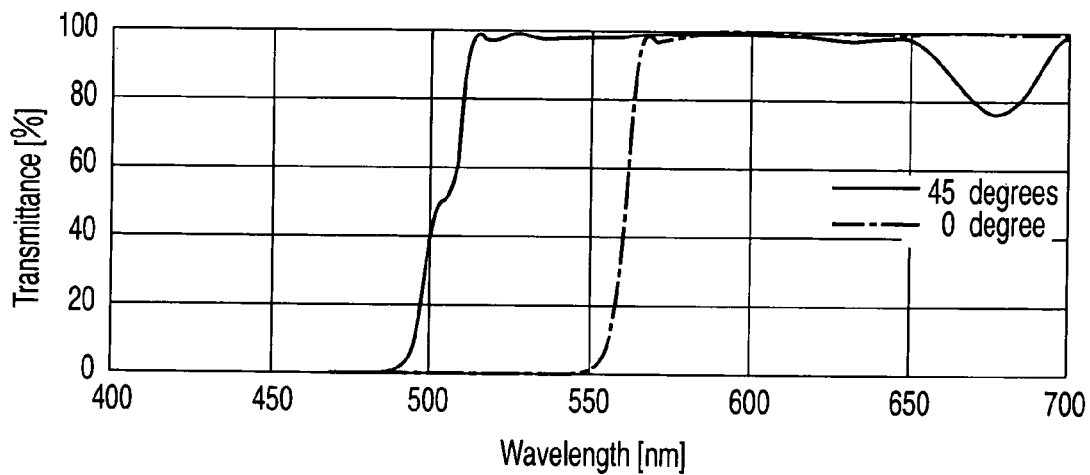
F I G. 16
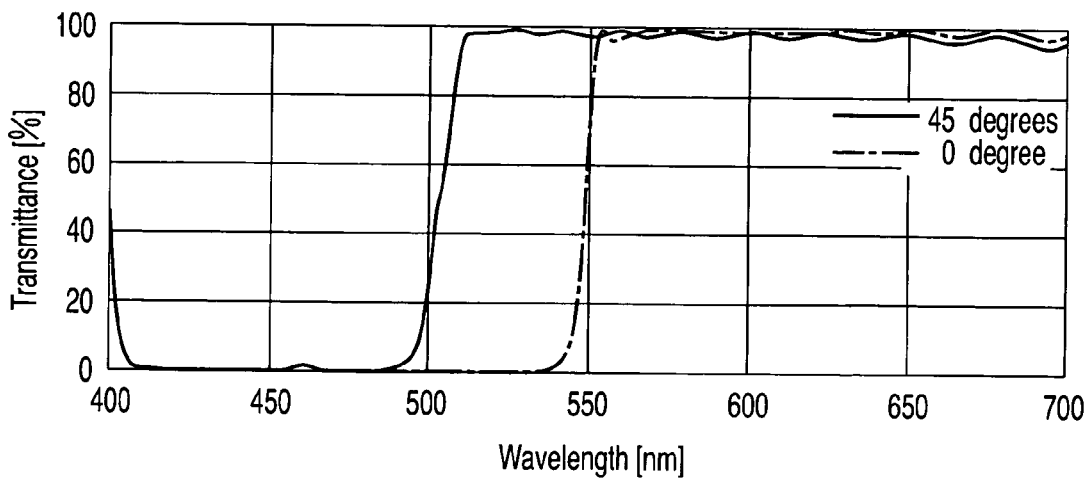
F I G. 17

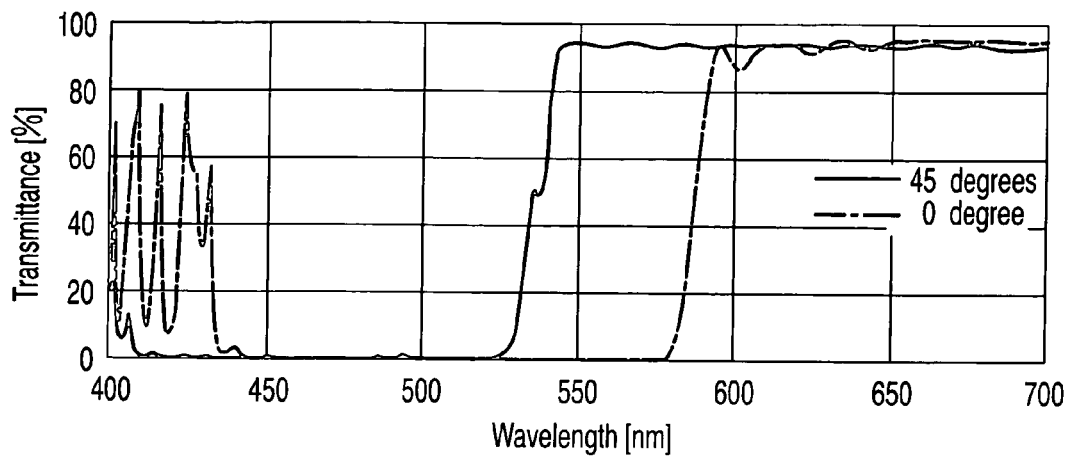
F I G. 18
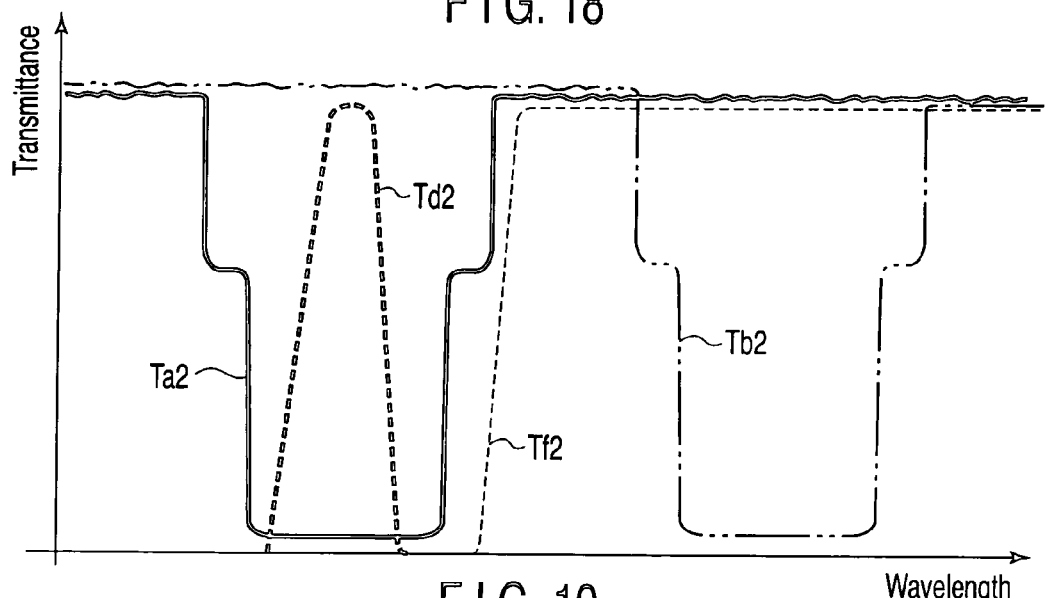
F I G. 19
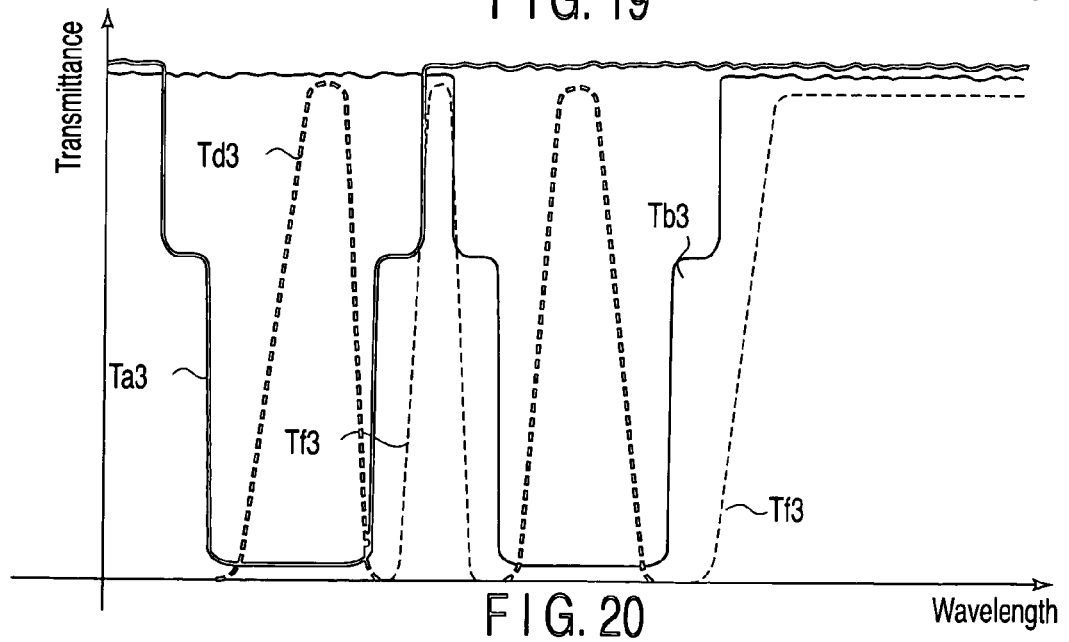
F I G. 20

EPI-ILLUMINATION MICROSCOPE AND FLUORESCENCE FILTER SET

CROSS-REFERENCE TO RELATED APPLICATIONS

This application is based upon and claims the benefit of priority from prior Japanese Patent Applications No. 2004-111356, filed Apr. 5, 2004; and No. 2004-355747, filed Dec. 8, 2004, the entire contents of both of which are incorporated herein by reference.

BACKGROUND OF THE INVENTION

1. Field of the Invention

The present invention relates to an epi-illumination microscope for use in observing light emitted from a sample.

2. Description of the Related Art

In general, a fluorescence observing epi-illumination microscope has been used for detecting fluorescence-labeled protein, tissue, gene and the like on a biological tissue cell in a biological or medical field. Especially, in recent years, a research of a micro sample having a level of one molecule that emits only feeble fluorescence, or a research using a living sample, not a fixed sample has been vigorously performed. Additionally, it is possible to develop light-emitting protein in the cell, detection or analysis has been possible while more physiological activity is kept. In a case where this living sample is observed, it has been demanded that fluorescence generated from the sample be efficiently detected with less irradiation energy while reducing noises entering an observation system as much as possible in order to reduce damages on the sample and correctly observe or analyze the sample. The feeble fluorescence having one molecule level cannot be detected until the noises that enter the observation system are minimized.

As one generation source of the noise, in general, there is a fluorescence filter set. FIG. 21 shows a constitution of a conventional microscope comprising the fluorescence filter set. As shown in FIG. 21, a fluorescence filter set 500 comprises three optical elements including an excitation filter 510, a light splitter 520, and an absorption filter 530. The excitation filter 510 selects only light having a predetermined wavelength from light from a light source 10 located off an optical axis of an optical observation system including an objective lens 30, an image forming lens 50, and a detection device 60. The light splitter 520 reflects the light having the wavelength selected by the excitation filter 510 to epi-illuminate a sample 40, and transmits the fluorescence generated from the sample 40 to guide it to the detection device 60. The light splitter 520 comprises a transparent substrate having a flat plate shape, the front surface of the transparent substrate is dichroic-mirror-coated, and the back surface thereof is coated with a reflection preventive film. The light splitter 520 is disposed with a tilt of 45 degrees with respect to an optical observation axis. The absorption filter 530 selectively excites the fluorescence transmitted through the light splitter 520, and cuts the wavelength light selected by the excitation filter 510. In general, the fluorescence filter set 500 is prepared for each wavelength of a fluorescent dyestuff.

In general, each of these optical elements (excitation filter 510, light splitter 520, absorption filter 530) comprises an interference filter whose parallel flat plate is coated with an interference film. Assuming that a maximum transmission wavelength is $\lambda$, an optical length of a dielectric is t, and a refractive angle in a boundary is $\phi$, an interference condition of the interference film is represented by $2t \cdot \cos \phi = m\lambda$.

Here, assuming that an order m is constant and an interference condition is constant, the wavelength $\lambda$ is proportional to $\cos \phi$. Although $\phi$ denotes the refractive angle, and is brought into a conjugated relation with respect to an incident angle by Snell's law, and both the angles are considered to be equal. Therefore, when the incident angle increases in the above equation, $\cos \phi$ decreases, the wavelength $\lambda$ also decreases, and a maximum transmittance portion gradually shifts to a short wavelength side. Therefore, when vertical incidence changes to oblique incidence, and the incident angle with respect to the interference film increases, a band opposite to a transmission band gradually shifts to the short wavelength side.

In the fluorescence filter set, the excitation filter and the absorption filter are designed to be optimum with respect to vertical incidence, and the light splitter is designed to be optimum with respect to 45 degree incidence. When the incident angle is different from a designed value, the wavelength light reflected at the incident angle having the designed value is transmitted, and the wavelength light transmitted at the incident angle having the designed value is reflected.

To perform efficient fluorescence observation, the light splitter may preferably completely reflect light of a transmission wavelength band of the excitation filter (first selection member), and completely transmit the light of a transmission wavelength band of the absorption filter (second selection member). However, a peak of an excitation wavelength of the fluorescent dyestuff, and that of an emission wavelength are near 10 to 20 mm in many cases. In general, a transmission band of the excitation filter (first selection member) can be brought close to that of the absorption filter (second selection member) to such an extent that the bands do not overlap with each other. However, when the light splitter is disposed at 45 degrees with respect to the optical axis, the light is separated with PS polarization. Therefore, unlike the transmission bands of the excitation filter (first selection member) and the absorption filter (second selection member), there is a limitation on thin-film design in bringing the transmission wavelength band close to a reflection wavelength band.

Moreover, when the band of the excitation wavelength of the fluorescent dyestuff is broad, the transmission wavelength band of the excitation filter (first selection member) is to be sometimes broadened. However, a conventional light splitter has a constitution in which one face of the transparent substrate is coated with a dichroic mirror having an only stacked portion for mainly reflecting the light transmitted through the excitation filter (first selection member), a film constitution is only changed, and there is a limitation to the broadening of the reflection band.

Exciting light is undesirably permitted to pass through the light splitter with respect to a certain wavelength band by these two factors. Therefore, the light that is not reflected by and is transmitted through the light splitter strikes on a side wall face of the fluorescence filter set, and is scattered by the side wall face. When this light ray enters the absorption filter at an angle deviating from the vertical incidence, even the light on a short wavelength side passes through the absorption filter unlike the vertical incidence, and this generates the noise. The light that has entered the side wall face of the fluorescence filter set emits self fluorescence, and even the self fluorescence emitted on the side of the absorption filter passes through the absorption filter.

Additionally, there is scattered light or self fluorescence generated when the excitation filter is irradiated with intense and broad-band light from the light source. A part of the scattered light or self fluorescence is emitted toward the light splitter or the absorption filter, but the incident angle of the light upon the light splitter approaches the vertical incidence from 45 device incidence indicating the designed value, and the incident angle upon the absorption filter turns to the oblique incidence from the vertical incidence indicating the designed value. That is, the reflection band of the light splitter shifts toward a long wavelength side, and the transmission band of the absorption filter shifts toward a short wavelength side. As a result, the scattered light or self fluorescence other than the light of the transmission band shifted toward the short wavelength side of the absorption filter and the long wavelength side of the light splitter passes through the light splitter or the absorption filter to generate the noise.

BRIEF SUMMARY OF THE INVENTION

A first aspect of the present invention is directed to an epi-illumination microscope. The epi-illumination microscope of the present invention comprises: a light source that emits light to illuminate a sample; a first wavelength selection member that selectively transmits the light from the light source; a light splitter that reflects the light from the first wavelength selection member to epi-illuminate the sample and transmits the light emitted from the sample; and a second wavelength selection member that selectively transmits the light transmitted through the light splitter, the light splitter comprising a transparent member and a dichroic mirror coat disposed on the transparent member, the dichroic mirror coat comprising a stacked layer that efficiently reflects light having a wavelength selected by the first wavelength selection member; and a stacked layer that reflects light on a short wavelength side from the light selected by the first wavelength selection member, light on a long wavelength side, light of the same band, or combined light.

In a more useful mode, this type of epi-illumination microscope comprises: a light source that emits light to illuminate a sample; a first wavelength selection member that selectively transmits the light from the light source; a light splitter that reflects the light from the first wavelength selection member to epi-illuminate the sample and transmits light emitted from the sample; and a second wavelength selection member that selectively transmits the light transmitted through the light splitter, the light splitter comprising a transparent member having first and second faces; a first dichroic mirror coat disposed on the first face; and a second dichroic mirror coat disposed on the second face.

A second aspect of the present invention is directed to a fluorescence filter set. The fluorescence filter set of the present invention comprises a first wavelength selection member that selectively transmits exciting light; a light splitter that reflects the exciting light from the first wavelength selection member to epi-illuminate a sample and transmits fluorescence emitted from the sample; and a second wavelength selection member that selectively transmits the fluorescence transmitted through the light splitter, the light splitter comprising a transparent member and a dichroic mirror coat disposed on the transparent member, the dichroic mirror coat comprising a stacked layer that efficiently reflects the light having a wavelength selected by the first wavelength selection member; and a stacked layer that reflects light on a short wavelength side from the light selected by the first wavelength selection member, light on a long wavelength side, light of the same band, or combined light.

In a more useful mode, this type of fluorescence filter set comprises: a first wavelength selection member that selectively transmits exciting light; a light splitter that reflects the exciting light from the first wavelength selection member to epi-illuminate the sample and transmits fluorescence emitted from the sample; and a second wavelength selection member that selectively transmits the fluorescence transmitted through the light splitter, the light splitter comprising a transparent member having first and second faces; a first dichroic mirror coat disposed on the first face; and a second dichroic mirror coat disposed on the second face.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 12 shows a spectral transmittance characteristic of a light splitter in which B of Table 1 is disposed as the first dichroic mirror coat, and D of Table 1 is disposed as the second dichroic mirror coat;

FIG. 13 shows a spectral transmittance characteristic of a light splitter in which C of Table 1 is disposed as the first dichroic mirror coat, and D of Table 1 is disposed as the second dichroic mirror coat;

FIG. 14 shows another light splitter applicable instead of the light splitter shown in FIG. 1, in which a transparent member comprises a bonded prism;

FIG. 15 shows spectral transmittance characteristics of first dichroic mirrors having film constitutions of a in Table 2;

FIG. 16 shows spectral transmittance characteristics of first dichroic mirrors having film constitutions of b in Table 2;

FIG. 17 shows spectral transmittance characteristics of first dichroic mirrors having film constitutions of a in Table 2;

FIG. 18 shows spectral transmittance characteristics of first dichroic mirrors having film constitutions of d in Table 2;

FIG. 19 shows a transmittance characteristic Td2 of a first wavelength selection member, a transmittance characteristic Ta2 of a first dichroic mirror coat disposed on the front surface of a flat-plate-like transparent substrate, and a transmittance characteristic Tb2 of a second dichroic mirror coat disposed on the back surface of the flat-plate-like transparent substrate in a fourth embodiment of the present invention;

FIG. 20 shows a transmittance characteristic Td3 of a first wavelength selection member, a transmittance characteristic Ta3 of a first dichroic mirror coat disposed on the front surface of a flat-plate-like transparent substrate, and a transmittance characteristic Tb3 of a second dichroic mirror coat disposed on the back surface of the flat-plate-like transparent substrate.

DETAILED DESCRIPTION OF THE INVENTION

Embodiments of the present invention will be described hereinafter with reference to the drawings.

FIRST EMBODIMENT

Figure 1:
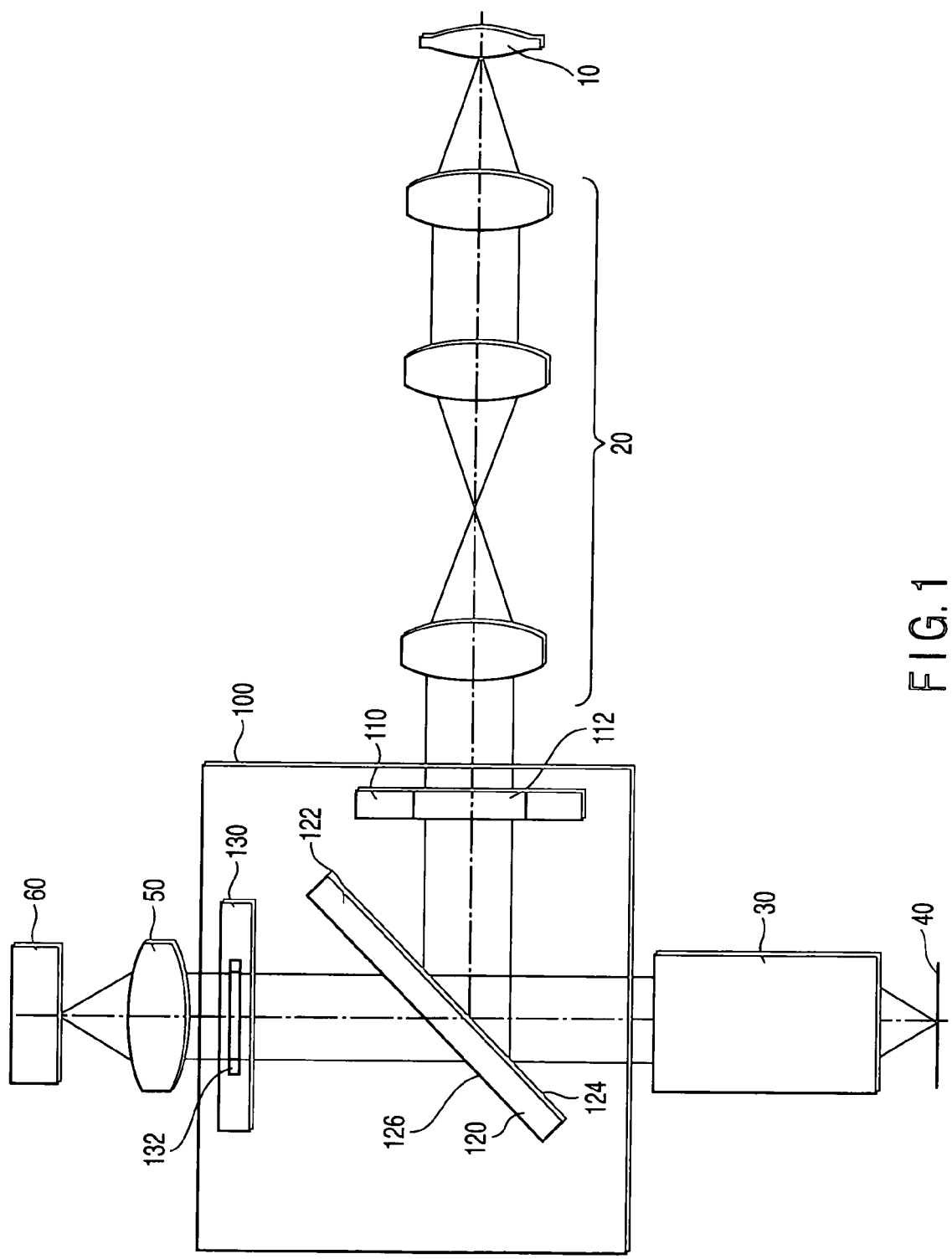
FIG. 1 shows a constitution of a microscope according to a first embodiment of the present invention.

The present embodiment relates to an upright microscope. FIG. 1 shows a constitution of a microscope according to a first embodiment of the present invention. As shown in FIG. 1, the microscope comprises a light source 10, an optical illumination system 20, a fluorescence filter set 100, an objective lens 30, an image forming lens 50, and a detection device 60.

The objective lens 30, image forming lens 50, and detection device 60 constitute an optical observation system that observes a sample 40. The light source 10, which is located off an optical axis of the optical observation system, emits light for illuminating the sample 40. The light source 10 is not limited to this, and comprises, for example, a mercury lamp.

The fluorescence filter set 100 comprises a first wavelength selection member 110, a light splitter 120, and a second wavelength selection member 130. The first wavelength selection member 110 functions as an excitation filter, and the second wavelength selection member 130 functions as an absorption filter.

The first wavelength selection member 110 comprises a first optical filter 112 having a predetermined wavelength characteristic, and the first optical filter 112 selectively transmits only light having a predetermined wavelength band. The second wavelength selection member 130 comprises a second optical filter 132 having a predetermined wavelength characteristic, and the second optical filter 132 selectively transmits only light having a predetermined wavelength band.

The light splitter 120 comprises a flat-plate-like transparent substrate 122, and dichroic mirror coats 124 and 126 are disposed on opposite surfaces of the flat-plate-like transparent substrate 122. That is, the light splitter 120 comprises: the flat-plate-like transparent substrate 122 that is a transparent member having a first face (front surface) and a second face (back surface); the first dichroic mirror coat 124 disposed on the front surface of the flat-plate-like transparent substrate 122; and the second dichroic mirror coat 126 disposed on the back surface of the flat-plate-like transparent substrate 122.

The light splitter 120 is disposed in such a manner as to form an angle of 45 degrees with respect to an optical axis of the optical illumination system 20. The front surface of the flat-plate-like transparent substrate 122 faces the first wavelength selection member 110 and the sample 40, and the back surface of the flat-plate-like transparent substrate 122 faces the second wavelength selection member 130.

In the present embodiment, the transparent member of the light splitter 120 comprises the flat-plate-like transparent substrate, but may comprise two flat-face-like substrates tilted by 22.5°, respectively, with respect to the optical axis.

Light emitted from the light source 10 includes light from an ultraviolet region to a near-infrared region. The light from the light source 10 passes through the optical illumination system 20 to strike on the first wavelength selection member 110. As to the light that has struck on the first wavelength selection member 110, only light having a predetermined wavelength band selected by the first optical filter 112 passes through the first wavelength selection member 110. The light transmitted through the first wavelength selection member 110, that is, exciting light strikes on the light splitter 120. The exciting light that has struck on the light splitter 120 is reflected toward the objective lens 30. The sample 40 is irradiated with the exciting light reflected by the light splitter 120 through the objective lens 30. In other words, the light splitter 120 reflects the light from the first wavelength selection member 110 to epi-illuminate the sample 40 through the objective lens 30.

The sample 40 irradiated with the exciting light emits fluorescence. A part of the exciting light is reflected by the sample 40. A part of the fluorescence generated from the sample 40, and a part of the exciting light reflected by the sample 40 enter the objective lens 30. That is, the light from the sample 40, collected by the objective lens 30, includes the fluorescence generated from the sample 40, and the exciting light reflected by the sample 40.

The fluorescence and the exciting light from the sample 40 pass through the objective lens 30 to strike on the light splitter 120. Within the light that has struck on the light splitter 120, the fluorescence passes through the light splitter 120, but most exciting light is reflected by the light splitter 120. That is, the light splitter 120 transmits the light emitted from the sample 40. The fluorescence transmitted through the light splitter 120 strikes on the second wavelength selection member 130. As to the light that has struck on the second wavelength selection member 130, only fluorescence selected by the second optical filter 132 is transmitted. The fluorescence transmitted through the second optical filter 132 is formed into an image in a predetermined position of the detection device 60 by the image forming lens 50 to form a fluorescent image of the sample 40. When an eyepiece lens is disposed near the image formed position of the fluorescent image, the fluorescent image can be visually observed. Since the fluorescent image is very dark, the image is usually picked up by an electronic imaging element such as a cooling CCD, especially an imaging element having high sensitivity.

Next, the light splitter 120 for use in the microscope of the present embodiment will be described.

Figure 2:
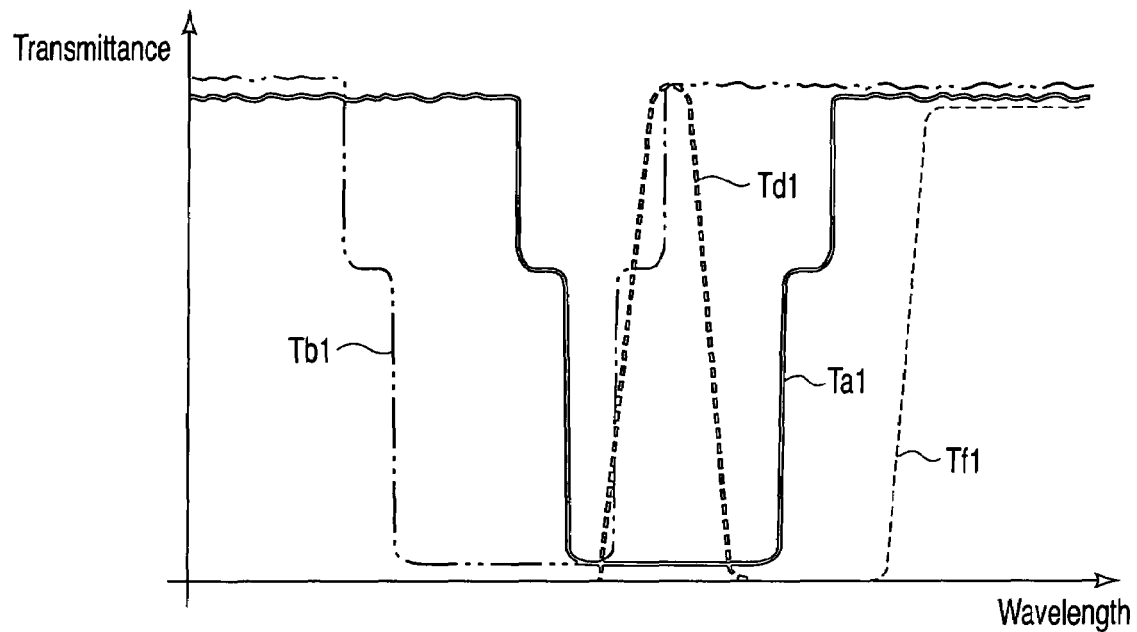
FIG. 2 shows a transmittance characteristic Td1 of a first wavelength selection member, a transmittance characteristic Ta1 of a first dichroic mirror coat disposed on the front surface of a transparent substrate having a flat plate shape, and a transmittance characteristic Tb1 of a second dichroic mirror coat disposed on the back surface of the transparent substrate having the flat plate shape in the first embodiment of the present invention.

As described above, the light splitter 120 comprises the flat-plate-like transparent substrate 122, the first dichroic mirror coat 124 disposed on the front surface of the flat-plate-like transparent substrate 122, and the second dichroic mirror coat 126 disposed on the back surface of the flat-plate-like transparent substrate 122. FIG. 2 shows a transmittance characteristic Td1 of the first wavelength selection member 110, a transmittance characteristic Ta1 of the first dichroic mirror coat 124 disposed on the front surface of the flat-plate-like transparent substrate 122, a transmittance characteristic Tb1 of the second dichroic mirror coat 126 disposed on the back surface of the flat-plate-like transparent substrate 122, and a transmittance characteristic Tf1 of the second wavelength selection member 130 in the first embodiment of the present invention.

As shown in FIG. 2, a transmission band of the transmittance characteristic Td1 of the first wavelength selection member 110 is positioned in a reflection band of the transmittance characteristic Ta1 of the first dichroic mirror coat 124. The reflection band of the transmittance characteristic Tb1 of the second dichroic mirror coat 126 is positioned on a short wavelength side from the reflection band of the transmittance characteristic Ta1 of the first dichroic mirror coat 124. Furthermore, the reflection band of the transmittance characteristic Ta1 of the first dichroic mirror coat 124 is partially superimposed upon that of the transmittance characteristic Tb1 of the second dichroic mirror coat 126. As a result, a whole reflection band of the light splitter 120 is broadened on the short wavelength side.

As seen from FIG. 2, the first dichroic mirror coat 124 reflects the exciting light transmitted through the first wavelength selection member 110. The second dichroic mirror coat 126 reflects the light on the short wavelength side with respect to the reflection band of the first dichroic mirror coat 124, and the exciting light that is transmitted through the first wavelength selection member 110 and is not reflected by the first dichroic mirror coat 124. Furthermore, the first dichroic mirror coat 124 and the second dichroic mirror coat 126 transmits the fluorescence emitted from the sample 40.

Figure 3:
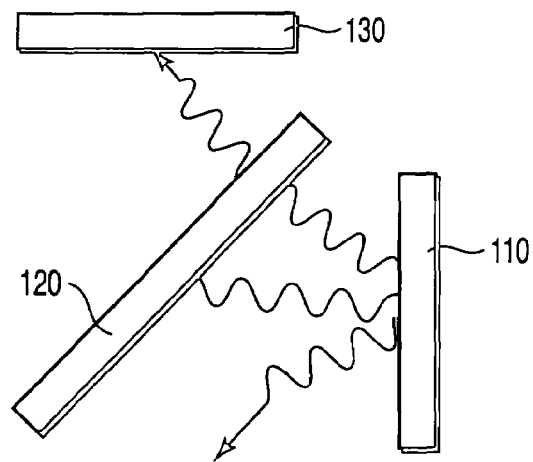
FIG. 3 shows a state in which light directed to a light splitter and a second wavelength selection member is generated by scattering by the first wavelength selection member.
Figure 4:
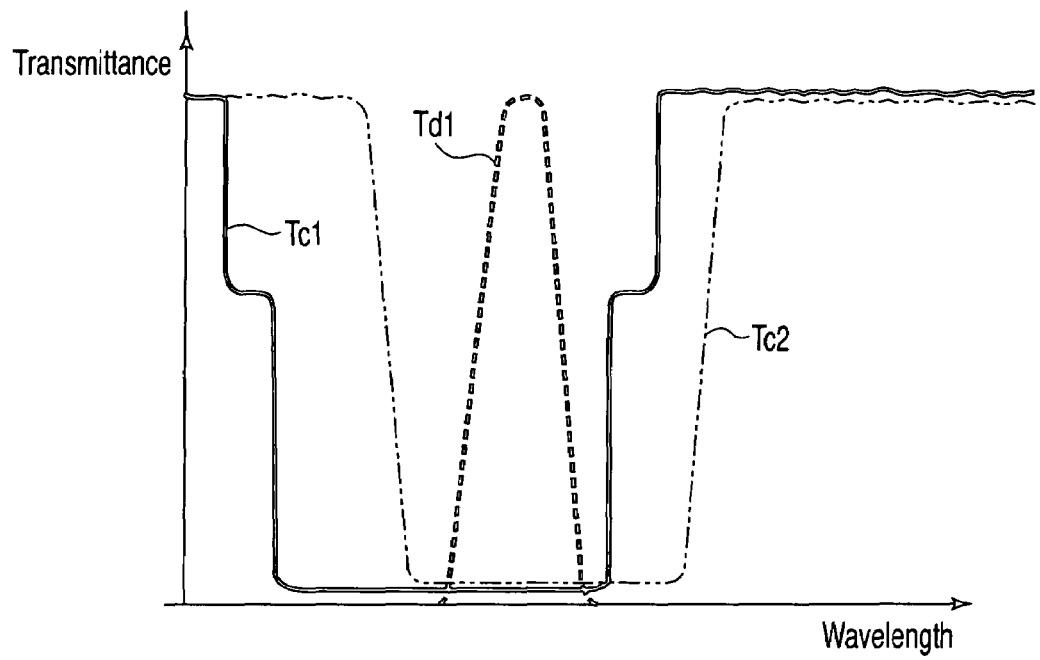
FIG. 4 shows the transmittance characteristic Td1 of the first wavelength selection member, a transmittance characteristic Tc1 of a light splitter of the first embodiment with respect to 45-degree incidence, and a transmittance characteristic Tc2 of the light splitter of the first embodiment with respect to 0-degree incidence (vertical incidence)
Figure 5:
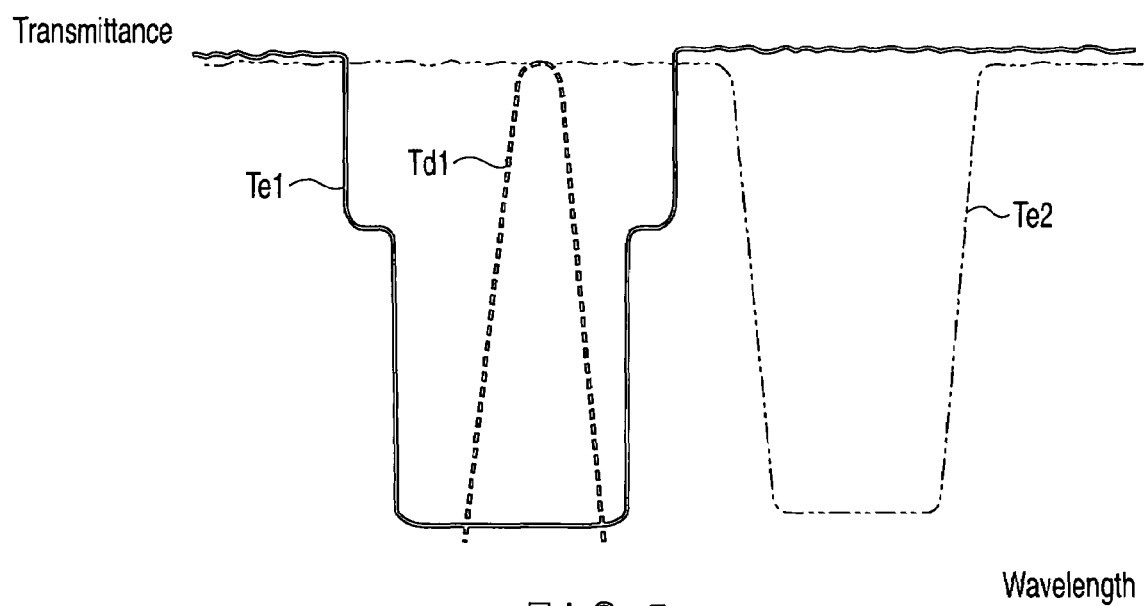
FIG. 5 shows the transmittance characteristic of the first wavelength selection member, that of a conventional light splitter with respect to the 45-degree incidence, and that of the conventional light splitter with respect to the 0-degree incidence (vertical incidence)

FIG. 3 shows a state in which light directed to the light splitter 120 and the second wavelength selection member 130 is generated by scattering by the first wavelength selection member 110. FIG. 4 shows the transmittance characteristic Td1 of the first wavelength selection member 110, a transmittance characteristic Tc1 of the light splitter 120 of the present embodiment with respect to 45-degree incidence, and a transmittance characteristic Tc2 of the light splitter 120 of the present embodiment with respect to 0-degree incidence (vertical incidence). FIG. 5 shows the transmittance characteristic of the first wavelength selection member 110, that of a conventional light splitter with respect to the 45-degree incidence, and that of the conventional light splitter with respect to the 0-degree incidence (vertical incidence).

As shown in FIG. 3, the light generated by the scattering by the first wavelength selection member 110 and directed toward the second wavelength selection member 130 is near vertical incidence with respect to the light splitter 120.

In the conventional light splitter, the dichroic mirror coat is disposed only on the front surface of the flat-plate-like transparent substrate, and the reflection band is secured by one dichroic mirror coat. Therefore, as shown in FIG. 5, the reflection band in the conventional light splitter includes the transmission band of the first wavelength selection member 110 in a transmittance characteristic Te1 with respect to the 45-degree incidence, and therefore the conventional light splitter reflects the light transmitted through the first wavelength selection member 110, that is, the exciting light. However, since the reflection band deviates from the transmission band of the first wavelength selection member 110 in a transmittance characteristic Te2 with respect to the 0-degree incidence (vertical incidence), the conventional light splitter transmits the light generated by the scattering on the first wavelength selection member 110 and directed toward the second wavelength selection member 130. Therefore, when the conventional light splitter is used, the light generated by the scattering on the first wavelength selection member 110 and directed toward the second wavelength selection member 130 is not reflected by the conventional light splitter, and reaches the second wavelength selection member 130.

On the other hand, since the reflection band is broadened on the short wavelength side as described above in the light splitter 120 of the present embodiment, as shown in FIG. 4, the reflection band includes the transmission band of the first wavelength selection member 110 not only in the transmittance characteristic Tc1 with respect to the 45-degree incidence but also in the transmittance characteristic Tc2 with respect to the 0-degree incidence. Therefore, the light generated by the scattering on the first wavelength selection member 110 and directed toward the second wavelength selection member 130 is reflected by the light splitter 120 of the present embodiment, and cannot reach the second wavelength selection member 130.

As in an example using the conventional light splitter, when the light scattered by the first wavelength selection member 110 passes through the light splitter to reach the second wavelength selection member 130, the light obliquely strikes on the second wavelength selection member, and therefore passes through the second wavelength selection member. This is because the transmittance characteristic Tf1 of the second wavelength selection member 130 shifts on the short wavelength side with respect to the obliquely entering light, and the light having the wavelength selected by the first wavelength selection member 110 is transmitted.

That is, when the light splitter 120 in the present embodiment is used, the light scattered by the first wavelength selection member 110 can be prevented from reaching the second wavelength selection member 130, and, as a result, an effect of reducing noises at a fluorescence observation time can be obtained.

Figure 6:
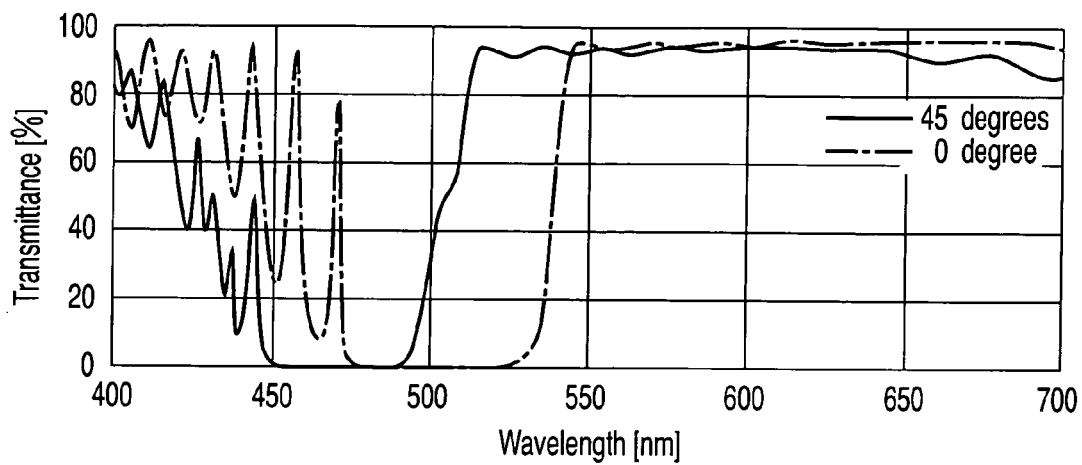
FIG. 6 shows a spectral transmittance characteristic of a first dichroic mirror having a film constitution of A of Table 1.

The first dichroic mirror coat 124 is preferably formed by stacking 20 or more layers of a high-refractive-index material having a refractive index of 2.0 or more, and a low-refractive-index material having a refractive index of 1.5 or less. In one example supposed to be preferable, an average optical film thickness of the high-refractive-index material is approximately $3\times\lambda/4$, and that of the low-refractive-index material is approximately $\lambda/4$ with respect to a central wavelength $\lambda$ of the light selected by the first wavelength selection member 110. In this case, the first dichroic mirror coat 124 has a reflection band near the wavelength $\lambda$, and has a transmission band on a long wavelength side from the reflection band. That is, the first dichroic mirror coat 124 includes a stacked layer that efficiently reflects the light having a wavelength $\lambda$ selected by the first wavelength selection member 110. An example of the corresponding first dichroic mirror coat 124 is a dichroic mirror coat having a film constitution in A of Table 1. Assuming that $\lambda$ is 475 nm, the average optical film thickness of the high-refractive-index material in the film constitution of the dichroic mirror coat is $3.15\times\lambda/4$, and that of the low-refractive-index material is $1.06\times\lambda/4$. That is, the average optical film thickness of the high-refractive-index material is $3\times\lambda/4$, and the average optical film thickness of the low-refractive-index material is approximately $\lambda/4$. The average optical film thickness in this example changes with selected $\lambda$, but preferably is in a range of 2.9 to 3.4 times while the average film thickness of the high-refractive-index material is $\lambda/4$, and is in a range of 0.9 to 1.2 times while the average film thickness of the low-refractive-index material is $\lambda/4$. A spectral transmittance characteristic of the first dichroic mirror coat having a film constitution of A of Table 1 is shown in FIG. 6.

TABLE 1

| | | Optical film thickness ($\times\lambda/4$) | | | |
|---|---|---|---|---|---|
| Layer | Film material (Substrate) | A ($\lambda$ = 475 nm) | B ($\lambda$ = 475 nm) | C ($\lambda$ = 483 nm) | D ($\lambda$ = 475 nm) |
| 1 | High-refractive-index material | 2.96 | 0.51 | 2.83 | 0.45 |
| 2 | Low-refractive-index material | 0.87 | 3.23 | 3.24 | 0.84 |
| 3 | High-refractive-index material | 3.11 | 1.38 | 3.15 | 0.94 |
| 4 | Low-refractive-index material | 1.07 | 3.18 | 3.33 | 0.94 |
| 5 | High-refractive-index material | 3.10 | 0.93 | 3.19 | 0.89 |
| 6 | Low-refractive-index material | 1.14 | 3.41 | 3.32 | 0.91 |
| 7 | High-refractive-index material | 3.11 | 1.17 | 3.21 | 0.99 |
| 8 | Low-refractive-index material | 1.15 | 3.23 | 3.33 | 1.02 |
| 9 | High-refractive-index material | 3.14 | 1.13 | 3.22 | 0.94 |
| 10 | Low-refractive-index material | 1.16 | 3.47 | 3.32 | 0.91 |
| 11 | High-refractive-index material | 3.13 | 0.87 | 3.23 | 0.97 |
| 12 | Low-refractive-index material | 1.16 | 3.49 | 3.33 | 1.05 |
| 13 | High-refractive-index material | 3.13 | 1.04 | 3.22 | 0.99 |
| 14 | Low-refractive-index material | 1.15 | 3.40 | 3.32 | 0.90 |
| 15 | High-refractive-index material | 3.12 | 0.98 | 3.22 | 0.90 |
| 16 | Low-refractive-index material | 1.15 | 3.23 | 3.30 | 1.06 |
| 17 | High-refractive-index material | 3.12 | 1.53 | 3.21 | 1.06 |
| 18 | Low-refractive-index material | 1.13 | 2.87 | 3.21 | 0.88 |
| 19 | High-refractive-index material | 3.11 | 1.56 | 3.26 | 0.78 |
| 20 | Low-refractive-index material | 1.17 | 3.32 | 1.64 | 1.14 |
| 21 | High-refractive-index material | 3.05 | 0.76 | — | 0.80 |
| 22 | Low-refractive-index material | 0.93 | 3.48 | — | 1.88 |
| 23 | High-refractive-index-material | 3.45 | 0.99 | — | — |
| 24 | Low-refractive-index material | 0.41 | 2.92 | — | — |
| 25 | High-refractive-index material | 3.38 | 1.57 | — | — |

TABLE 1-continued

| | | Optical film thickness (×λ/4) | | | |
|---|---|---|---|---|---|
| Layer | Film material (Substrate) | A (λ = 475 nm) | B (λ = 475 nm) | C (λ = 483 nm) | D (λ = 475 nm) |
| 26 | Low-refractive-index material | 1.32 | 1.31 | — | — |

\* The constitution of the film is shown in order from the side of the flat-plate-like transparent substrate 120.
\* The optical film thickness is shown in a multiple number of λ/4.

Figure 7:
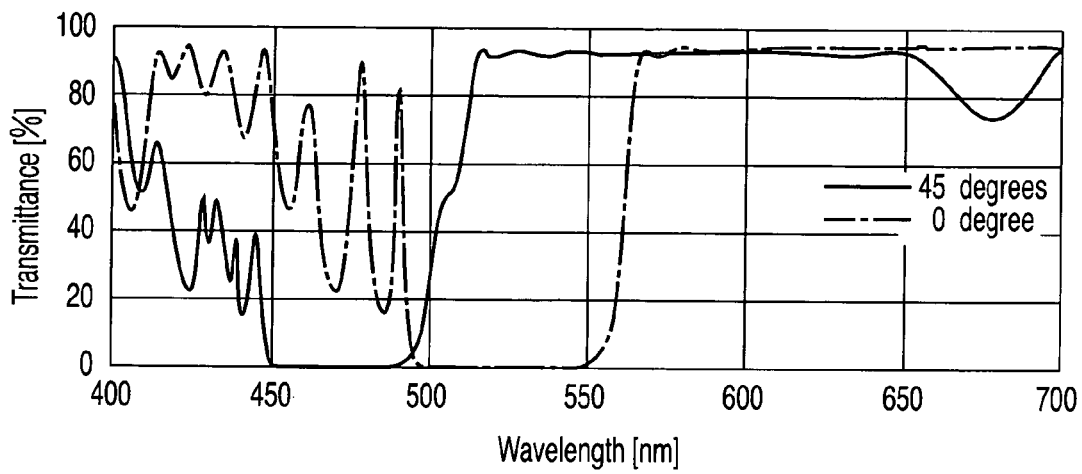
FIG. 7 shows a spectral transmittance characteristic of a first dichroic mirror having a film constitution of B of Table 1.

In another example supposed to be preferable, an average optical film thickness of the high-refractive-index material is approximately λ/4, and that of the low-refractive-index material is approximately 3×λ/4. In this case, the first dichroic mirror coat 124 has a reflection band near the wavelength λ, and has a transmission band on a long wavelength side from the reflection band. That is, the first dichroic mirror coat 124 includes a stacked layer that efficiently reflects the light having a wavelength λ selected by the first wavelength selection member 110. An example of the corresponding first dichroic mirror coat 124 is a dichroic mirror coat having a film constitution in B of Table 1. Assuming that λ is 475 nm, the average optical film thickness of the high-refractive-index material in the film constitution of the dichroic mirror coat is 1.11×λ/4, and that of the low-refractive-index material is 3.12×λ/4. That is, the average optical film thickness of the high-refractive-index material is approximately λ/4, and the average optical film thickness of the low-refractive-index material is approximately 3×λ/4. The average optical film thickness in this example changes with selected λ, but is preferably in a range of 0.9 to 1.2 times while the average film thickness of the high-refractive-index material is λ/4, and is in a range of 2.9 to 3.4 times while the average film thickness of the low-refractive-index material is λ/4. A spectral transmittance characteristic of the first dichroic mirror coat having a film constitution of B of Table 1 is shown in FIG. 7.

According to the first dichroic mirror coat 124, separation of PS-polarization generated in a case where the light splitter 120 is disposed at 45 degrees with respect to the optical axis can be reduced. Therefore, the light splitter 120 can efficiently reflect the light of the wavelength band selected by the first wavelength selection member 110, and efficiently transmit the light of the wavelength band selected by the second wavelength selection member 130.

Figure 8:
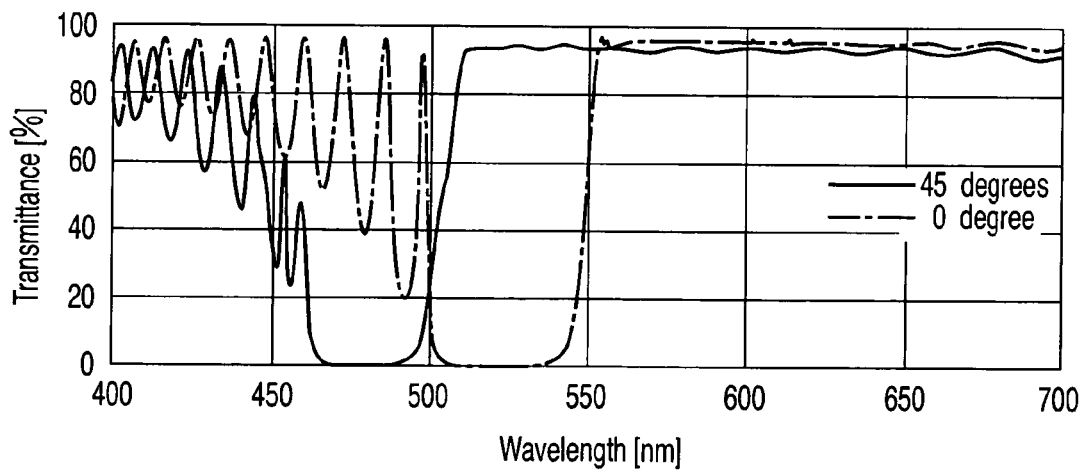
FIG. 8 shows a spectral transmittance characteristic of a first dichroic mirror having a film constitution of C of Table 1.

In still another example, an average optical film thickness of the high-refractive-index material is approximately 3×λ/4, and that of the low-refractive-index material is approximately 3×λ/4. In this case, the first dichroic mirror coat 124 has a reflection band near the wavelength λ, and has a transmission band generated on a long wavelength side from the reflection band. That is, the first dichroic mirror coat 124 includes a stacked layer that efficiently reflects the light having a wavelength λ selected by the first wavelength selection member 110. An example of the corresponding first dichroic mirror coat 124 is a dichroic mirror coat having a film constitution in C of Table 1. Assuming that λ is 483 nm, the average optical film thickness of the high-refractive-index material in the film constitution of the dichroic mirror coat is 3.18×λ/4, and that of the low-refractive-index material is 3.14×λ/4. That is, the average optical film thickness of the high-refractive-index material is approximately 3×λ/4, and the average optical film thickness of the low-refractive-index material is approximately 3×λ/4. A preferable range of the average optical film thickness in this example changes with selected λ, but is in a range of 2.9 to 3.4 times while the average film thickness of the high-refractive-index material is λ/4, and is in a range of 2.9 to 3.4 times while the average film thickness of the low-refractive-index material is λ/4. A spectral transmittance characteristic of the first dichroic mirror coat having a film constitution of C of Table 1 is shown in FIG. 8.

According to the first dichroic mirror coat 124, separation of PS-polarization generated in a case where the light splitter is disposed at 45 degrees with respect to the optical axis can be reduced as compared with the above-described two examples.

Figure 9:
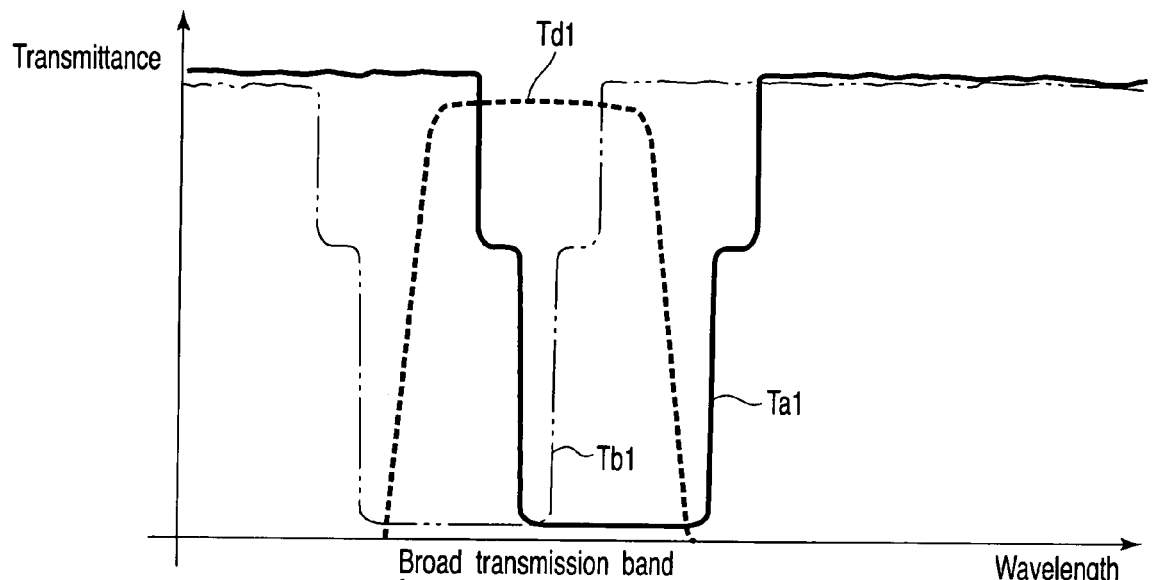
FIG. 9 shows spectral transmittance characteristics Ta1 and Tb1 of two dichroic mirror coats of a light splitter whose reflection band is broadened, and a transmittance characteristic Td1 of a first wavelength selection member having a broad transmission band applicable to the light splitter.

The light splitter 120 can secure the reflection band by two dichroic mirror coats: the first dichroic mirror coat 124 disposed on the front surface of the flat-plate-like transparent substrate 122; and the second dichroic mirror coat 126 disposed on the back surface of the flat-plate-like transparent substrate 122. Therefore, it is possible to broaden the reflection band of the light splitter 120. Accordingly, it is possible to apply a member having a transmittance characteristic that the transmission band is broad to the first wavelength selection member 110 (e.g., a case shown in FIG. 9). The light splitter 120 efficiently transmits the fluorescence generated from the sample 40, but most of quantity of exciting light transmitted through the light splitter 120 can be eliminated, and therefore the generation of the noise can be reduced by the above-described function. The present invention is also applicable to a case where a member having a transmittance characteristic of an ultra broad band is applied to the first wavelength selection member 110.

Figure 10:
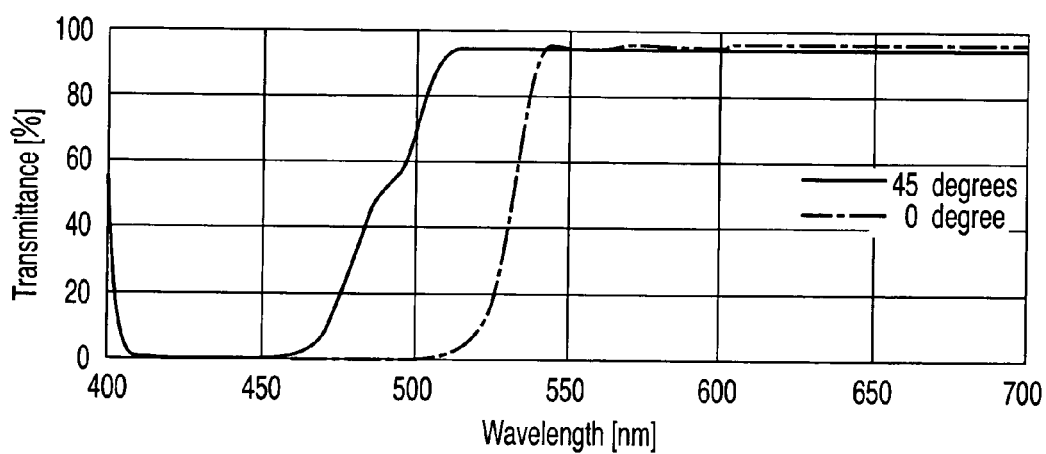
FIG. 10 shows a spectral transmittance characteristic of a second dichroic mirror having a film constitution of D of Table 1.

The second dichroic mirror coat 126 is preferably formed by stacking 20 or more layers of a high-refractive-index material having a refractive index of 2.0 or more, and a low-refractive-index material having a refractive index of 1.5 or less. In one example supposed to be preferable, an average optical film thickness of the high-refractive-index material is approximately λ/4, and that of the low-refractive-index material is approximately λ/4 with respect to a central wavelength λ of the light selected by the first wavelength selection member 110. In this case, the second dichroic mirror coat 126 has a reflection band near the wavelength λ, and has a transmission band on a long wavelength side from the reflection band. That is, the second dichroic mirror coat 126 includes a stacked layer that reflects light on a short wavelength side from the light selected by the first wavelength selection member 110, light on a long wavelength side, or combined light. An example of the corresponding second dichroic mirror coat 126 is a dichroic mirror coat having a film constitution in D of Table 1. Assuming that λ is 475 nm, the average optical film thickness of the high-refractive-index material in the film constitution of the dichroic mirror coat is 0.93×λ/4, and that of the low-refractive-index material is 0.96×λ/4. That is, the average optical film thickness of the high-refractive-index material is approximately λ/4, and the average optical film thickness of the low-refractive-index material is approximately λ/4. The average optical film thickness in this example changes with selected λ, but is preferably in a range of 0.8 to 1.1 times while the average film thickness of the high-refractive-index material is λ/4, and is in a range of 0.8 to 1.1 times while the average film thickness of the low-refractive-index material is λ/4. A spectral transmittance characteristic of the second dichroic mirror coat having a film constitution of D of Table 1 is shown in FIG. 10.

Figure 11:
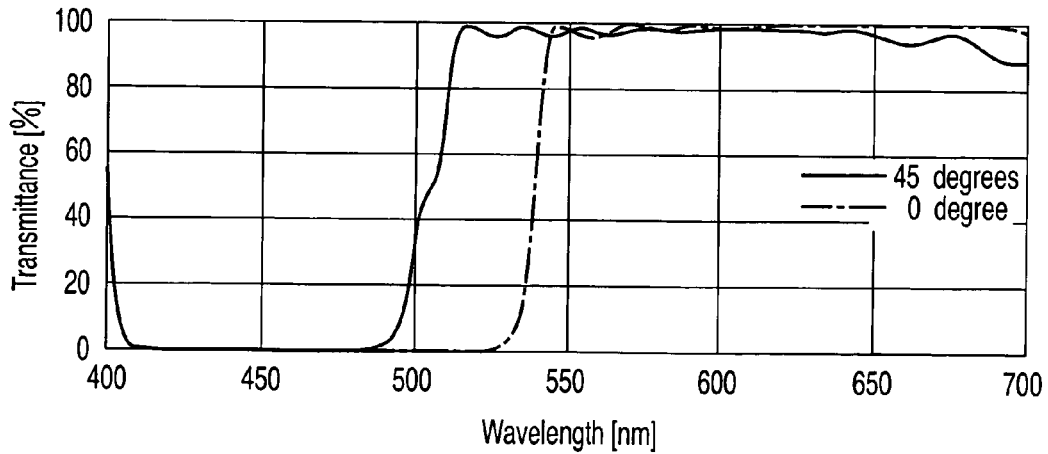
FIG. 11 shows a spectral transmittance characteristic of a light splitter in which A of Table 1 is disposed as a first dichroic mirror coat, and D of Table 1 is disposed as a second dichroic mirror coat.
Figure 21:
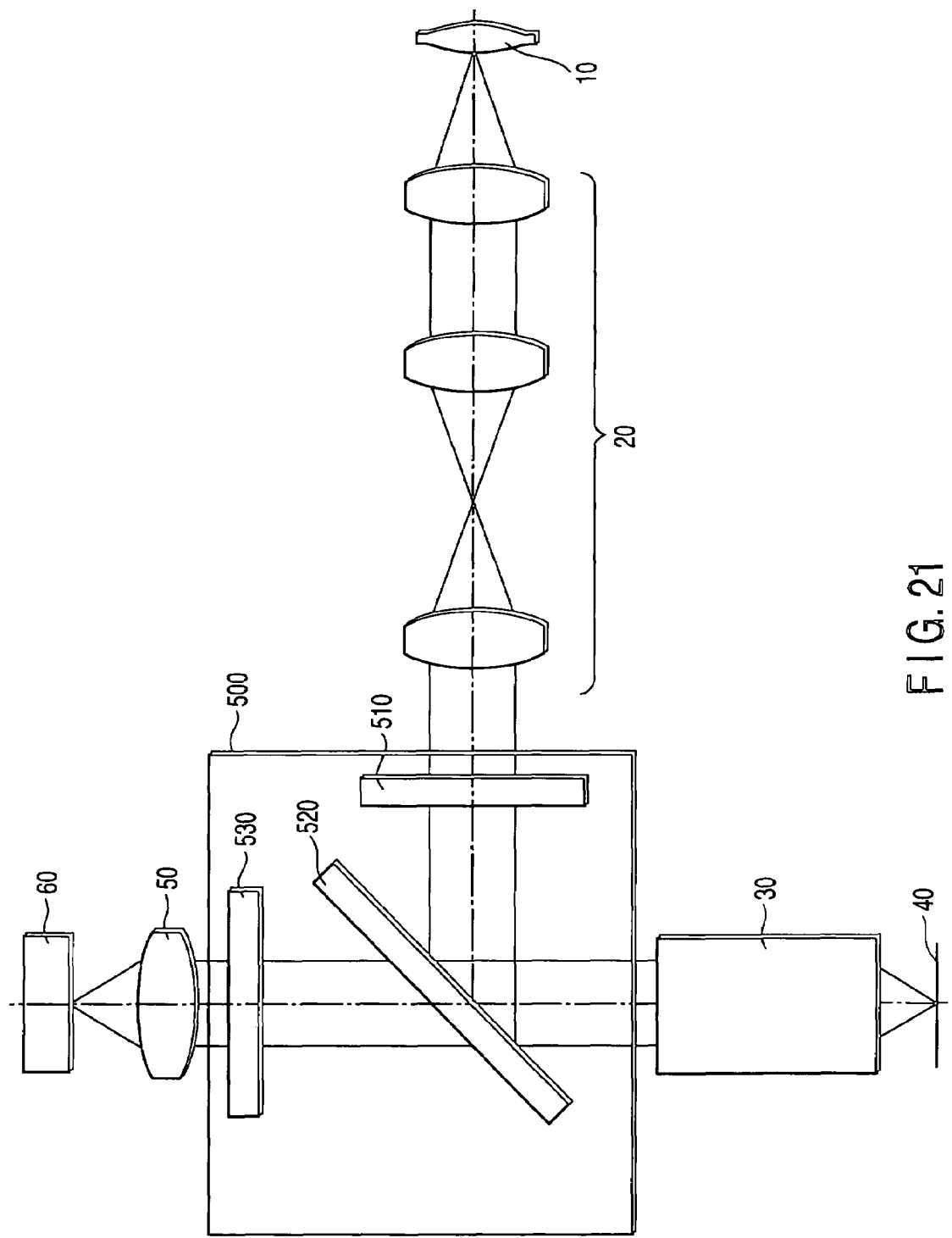
FIG. 21 shows a constitution of a conventional microscope comprising a fluorescence filter set.

Additionally, spectral transmittance characteristics of the light splitter 120 comprising the first dichroic mirror coat 124 and the second dichroic mirror coat 126 are shown in FIGS. 11, 12, 13. FIG. 11 shows an example in which A of Table 1 indicating that an average optical film thickness of a high-refractive-index material is approximately λ/4, and that of a low-refractive-index material is approximately 3×λ/4 is disposed as the first dichroic mirror coat 124, and D of Table 1 indicating that the average optical film thickness of the high-refractive-index material is approximately λ/4 and that of the low-refractive-index material is approximately λ/4 is disposed as the second dichroic mirror coat 126. FIG. 12 shows an example in which B of Table 1 indicating that an average optical film thickness of a high-refractive-index material is approximately 3×λ/4 and that of a low-refractive-index material is approximately λ/4 is disposed as the first dichroic mirror coat 124, and D of Table 1 indicating that the average optical film thickness of the high-refractive-index material is approximately λ/4 and that of the low-refractive-index material is approximately λ/4 is disposed as the second dichroic mirror coat 126. FIG. 13 shows an example in which C of Table 1 indicating that an average optical film thickness of a high-refractive-index material is approximately 3×λ/4 and that of a low-refractive-index material is approximately 3×λ/4 is disposed as the first dichroic mirror coat 124, and D of Table 1 indicating that the average optical film thickness of the high-refractive-index material is approximately λ/4 and that of the low-refractive-index material is approximately λ/4 is disposed as the second dichroic mirror coat 126. In any example, the light having a wavelength λ (in the vicinity of 375 nm) is not transmitted in the 0-degree incidence.

An optical element using color glass that satisfactorily absorbs the light having the wavelength selected by the first wavelength selection member 110 in the substrate is applied to the second wavelength selection member 130 in many cases in order to reduce noises by obliquely incident light. However, in the present embodiment, since the light splitter 120 also satisfactorily interrupts the light generated by the scattering on the first wavelength selection member 110 and directed to the second wavelength selection member 130, the optical element using color glass that satisfactorily absorbs the obliquely incident light in the substrate does not have to be applied to the second wavelength selection member 130.

Since color glass does not have dependence of a spectral characteristic on an angle, color glass alone of a long wavelength side transmission and short wavelength side absorption type or band pass type may constitute the absorption filter, or the excitation filter may be constituted by disposing an interference film on color glass.

However, in a case where color glass alone constitutes the absorption filter, fluctuations of the spectral characteristic of color glass are large, and an absorption band of color glass is not brought near the transmission band. Therefore, the fluorescence dyestuff is excited with a wavelength deviating from the exciting wavelength of the fluorescence having a best observation efficiency, and an emission wavelength peak, and the fluorescence emitted from the dyestuff has to be observed. Therefore, efficient fluorescence observation cannot be performed.

Moreover, a case where the interference film is disposed on color glass is strong even against oblique incidence. In the vertical incidence, the peak of the emission wavelength of the fluorescence can be easily grasped by the characteristic of the interference film. However, since color glass itself easily emits self fluorescence as compared with general optical glass, noises are easily generated.

Furthermore, in recent years, for an environmental measure, switching to glass called eco glass and constituted without toxic materials such as arsenic, lead, chromium, and cadmium has been promoted. However, it is difficult to constitute color glass without any toxic material. Therefore, as long as color glass is used, a glass member of the microscope cannot comprise only eco glass that is friendly to global environment.

In the present embodiment, an optical element using color glass does not have to be applied to the second wavelength selection member 130. As a result, efficient fluorescence observation can be performed with less noise. Furthermore, an optical element using eco glass in the substrate is applicable to the second wavelength selection member 130. As a result, the glass member of the microscope can comprise only eco glass friendly to global environment.

The first dichroic mirror coat 124 and the second dichroic mirror coat 126 usually comprise interference films. As to film thicknesses of the first dichroic mirror coat 124 and the second dichroic mirror coat 126, a ratio of the film thickness (physical film thickness of the first dichroic mirror coat 124 divided by that of the second dichroic mirror coat 126) may be preferably larger than ⅓ and smaller than 3. That is, the film thickness of the first dichroic mirror coat 124 may be close to that of the second dichroic mirror coat 126.

In the conventional light splitter, the dichroic mirror coat is disposed on the front surface of the flat-plate-like transparent substrate, and a reflection preventive film is disposed on the back surface thereof. The number of layers of the dichroic mirror coat is usually 20 or more, and the number of layers of the reflection preventive film is 1 to 9. Since a difference between both the film thicknesses is large, a difference of stress between the films is large. As a result, the flat-plate-like transparent substrate sometimes warps. The warpage of the flat-plate-like transparent substrate adversely affects illumination or observation performances.

On the other hand, in the light splitter 120 of the present invention, a difference between the film thickness of the first dichroic mirror coat 124 disposed on the front surface of the flat-plate-like transparent substrate 122 and that of the second dichroic mirror coat 126 disposed on the back surface of the flat-plate-like transparent substrate 122 is comparatively small. Therefore, a stress by the interference film constituting the first dichroic mirror coat 124 and that by the interference film constituting the second dichroic mirror coat 126 are substantially offset. Accordingly, the generation of the warpage of the flat-plate-like transparent substrate 122 that is a transparent member is inhibited. This enhances the illumination and observation performances.

SECOMD EMBODIMENT

A whole constitution of an epi-illumination microscope according to a second embodiment of the present invention is substantially the same as that of the first embodiment, and is therefore as shown in FIG. 1. However, the light splitter 120 of the present embodiment is different from that of the first embodiment in that a dichroic mirror coat 124 is disposed on the front surface of a flat-plate-like transparent substrate 122, and a reflection preventive film 126 is disposed on the back surface.

The dichroic mirror coat on the front surface is preferably formed by stacked layers of a high-refractive-index material having a refractive index of 2.0 or more and a low-refractive-index material having a refractive index of 1.5 or less in the same manner as in the dichroic mirror coat in the first embodiment. Among the materials, the coat comprises a stacked layer that efficiently reflects the light having the wavelength selected by the first wavelength selection member 110, and a stacked layer that reflects the light on a short wavelength side from the light selected by the first wavelength selection member. As a result, the only dichroic mirror coat 124 on the front surface realizes the transmittance characteristic equal to that of the light splitter in the first embodiment.

The reflection preventive film on the back surface is disposed for a purpose of inhibiting reflection of light generated on the back surface.

That is, unlike the first embodiment, the opposite surfaces of the light splitter of the present embodiment do not comprise the dichroic mirror coats, and the only dichroic mirror coat disposed on the front surface splits light in the same manner as in the conventional light splitter. However, the conventional light splitter comprises the only stacked layer that reflects the light having the wavelength selected by the first wavelength selection member. On the other hand, in the light splitter of the present embodiment, the stacked layer that efficiently reflects the light having the wavelength selected by the first wavelength selection member, and the stacked layer that reflects the light on the short wavelength side from the light selected by the first wavelength selection member are disposed on the dichroic mirror coat on the front surface, accordingly a light splitter having a broad reflection band is realized, and the present embodiment is different from the conventional light splitter in this respect.

In the present embodiment, the transparent member of the light splitter 120 comprises the flat-plate-like transparent substrate, but may comprise two flat-face-like substrates tilted by 22.5°, respectively, with respect to an optical axis. Alternatively, a dichroic mirror coat 128 according to the present embodiment may be disposed on a bonded face between bonded prisms as shown in FIG. 14.

In the light splitter 120 in the present embodiment, as described above, the dichroic mirror coat 124 is disposed on the front surface of the flat-plate-like transparent substrate 122, the reflection preventive film 126 is disposed on the back surface thereof, and the dichroic mirror coat 124 on the front surface comprises the stacked layer that efficiently reflects the light having the wavelength selected by the first wavelength selection member 110, and the stacked layer that reflects the light on the short wavelength side from the light selected by the first wavelength selection member. The transmittance characteristic of the light splitter of the present embodiment is equivalent to that shown in FIG. 4 referred to in the description of the first embodiment. Since the reflection band is broadened on the short wavelength side, the reflection band includes a transmission band of the first wavelength selection member 110 not only in a transmittance characteristic Tc1 with respect to 45-degree incidence but also in a transmittance characteristic Tc2 with respect to 0-degree incidence. Therefore, the light generated by the scattering on the first wavelength selection member 110 and directed toward the second wavelength selection member 130 is reflected by the light splitter 120 of the present embodiment, and cannot reach the second wavelength selection member 130.

That is, by the use of the light splitter 120 in the present embodiment, the light scattered by the first wavelength selection member 110 can be prevented from reaching the second wavelength selection member 130. As a result, a noise reducing effect at a fluorescence observation time can be obtained.

As described above, the dichroic mirror coat 124 of the present embodiment is preferably formed by the stacked layers of the high-refractive-index material having a refractive index of 2.0 or more, and the low-refractive-index material having a refractive index of 1.5 or less. In a preferable example, the coat comprises 14 or more stacked layers that efficiently reflects the light having the wavelength selected by the first wavelength selection member 110, and 14 or more stacked layer that reflect the light on the short wavelength side from the light selected by the first wavelength selection member. In one example supposed to be preferable, the dichroic mirror coat 124 of the present embodiment comprise: stacked layers that efficiently reflect light of $\lambda$ and in which an average optical film thickness of a high-refractive-index material is approximately $3\times\lambda/4$ and that of a low-refractive-index material is approximately $\lambda/4$ with respect to a central wavelength $\lambda$ of the light selected by the first wavelength selection member; and stacked layers that reflect the light on the short wavelength side from the light selected by the first wavelength selection member and in which the average optical film thickness of the high-refractive-index material is approximately $\lambda/4$, and that of the low-refractive-index material is approximately $\lambda/4$. In this case, the dichroic mirror coat 124 has a reflection band near the wavelength $\lambda$, a reflection band broadened on the short wavelength side, and a transmission band on a long wavelength side from the reflection band. Examples of the corresponding dichroic mirror coat 124 include dichroic mirror coats having film constitutions in a of Table 2, and dichroic mirror coats having film constitutions in b of Table 2. In the film constitutions of the dichroic mirror coats of a of Table 2, 23 to 40 stacked layers efficiently reflect the central wavelength $\lambda$ of the light selected by the first wavelength selection member. Assuming that $\lambda$ is 475 nm, an average optical film thickness of the high-refractive-index material is approximately $3.15\times\lambda/4$, and that of the low-refractive-index material is approximately $1.12\times\lambda/4$. Moreover, 5 to 20 stacked layers reflect the light on the short wavelength side from the central wavelength $\lambda$ of the light selected by the first wavelength selection member. Assuming that $\lambda$ is 475 nm in the same manner as described above, an average optical film thickness of the high-refractive-index material is approximately $0.93\times\lambda/4$, and that of the low-refractive-index material is approximately $0.94\times\lambda/4$. Similarly, in the film constitutions of the dichroic mirror coats of b in Table 2, 45 to 58 stacked layers efficiently reflect the central wavelength $\lambda$ of the light selected by the first wavelength selection member. Assuming that $\lambda$ is 580 nm, an average optical film thickness of the high-refractive-index material is approximately $3.16\times\lambda/4$, and that of the low-refractive-index material is approximately $1.16\times\lambda/4$. Moreover, 23 to 40 stacked layers reflect the light on the short wavelength side from the central wavelength $\lambda$ of the light selected by the first wavelength selection member. Assuming that $\lambda$ is 580 nm in the same manner as described above, an average optical film thickness of the high-refractive-index material is approximately $0.94\times\lambda/4$, and that of the low-refractive-index material is approximately $0.95\times\lambda/4$.

TABLE 2

| Layer | Film material (Substrate) | Optical film thickness (×λ/4) | | | |
|---|---|---|---|---|---|
| | | a (λ = 475 nm) | b (λ = 580 nm) | c (λ = 490 nm) | d (λ = 515 nm) |
| 1 | High-refractive-index material | 2.81 | 2.37 | 0.58 | 2.7 |
| 2 | Low-refractive-index material | 1.15 | 2.78 | 0.86 | 1.63 |
| 3 | High-refractive-index material | 0.62 | 0.45 | 0.87 | 0.45 |
| 4 | Low-refractive-index material | 0.96 | 0.79 | 0.96 | 0.99 |
| 5 | High-refractive-index material | 0.93 | 0.77 | 0.96 | 0.95 |
| 6 | Low-refractive-index material | 0.94 | 0.79 | 0.95 | 0.96 |
| 7 | High-refractive-index material | 0.93 | 0.77 | 0.96 | 0.95 |
| 8 | Low-refractive-index material | 0.94 | 0.79 | 0.95 | 0.96 |
| 9 | High-refractive-index material | 0.93 | 0.77 | 0.96 | 0.95 |
| 10 | Low-refractive-index material | 0.94 | 0.79 | 0.95 | 0.96 |
| 11 | High-refractive-index material | 0.93 | 0.77 | 0.96 | 0.95 |
| 12 | Low-refractive-index material | 0.94 | 0.79 | 0.95 | 0.96 |
| 13 | High-refractive-index material | 0.93 | 0.77 | 0.96 | 0.95 |
| 14 | Low-refractive-index material | 0.94 | 0.79 | 0.95 | 0.96 |
| 15 | High-refractive-index material | 0.93 | 0.77 | 0.96 | 0.95 |
| 16 | Low-refractive-index material | 0.94 | 0.79 | 0.95 | 0.96 |
| 17 | High-refractive-index material | 0.93 | 0.77 | 0.96 | 0.95 |
| 18 | Low-refractive-index material | 0.94 | 0.79 | 0.68 | 0.96 |
| 19 | High-refractive-index material | 0.93 | 0.84 | 1.27 | 0.95 |
| 20 | Low-refractive-index material | 0.94 | 0.98 | 3.32 | 0.96 |
| 21 | High-refractive-index material | 0.87 | 0.78 | 1.01 | 0.95 |
| 22 | Low-refractive-index material | 0.98 | 0.91 | 3.21 | 0.96 |
| 23 | High-refractive-index material | 3.3 | 0.94 | 1.17 | 0.95 |
| 24 | Low-refractive-index material | 0.99 | 0.95 | 3.21 | 0.96 |
| 25 | High-refractive-index material | 3.13 | 0.94 | 1.17 | 0.88 |
| 26 | Low-refractive-index material | 1.14 | 0.95 | 3.21 | 0.87 |
| 27 | High-refractive-index material | 3.13 | 0.94 | 1.17 | 3.5 |
| 28 | Low-refractive-index material | 1.14 | 0.95 | 3.21 | 0.72 |
| 29 | High-refractive-index material | 3.13 | 0.94 | 1.17 | 3.3 |
| 30 | Low-refractive-index material | 1.14 | 0.95 | 3.21 | 3.28 |
| 31 | High-refractive-index material | 3.13 | 0.94 | 1.17 | 3.3 |
| 32 | Low-refractive-index material | 1.14 | 0.95 | 3.21 | 3.28 |
| 33 | High-refractive-index material | 3.13 | 0.94 | 1.17 | 3.3 |
| 34 | Low-refractive-index material | 1.14 | 0.95 | 3.21 | 3.28 |
| 35 | High-refractive-index material | 3.13 | 0.94 | 1.17 | 3.3 |
| 36 | Low-refractive-index material | 1.14 | 0.95 | 3.21 | 3.28 |
| 37 | High-refractive-index material | 3.13 | 0.94 | 1.17 | 3.3 |

TABLE 2-continued

| Layer | Film material (Substrate) | Optical film thickness (×λ/4) | | | |
|---|---|---|---|---|---|
| | | a ($\lambda$ = 475 nm) | b ($\lambda$ = 580 nm) | c ($\lambda$ = 490 nm) | d ($\lambda$ = 515 nm) |
| 38 | Low-refractive-index material | 1.14 | 0.95 | 3.21 | 3.28 |
| 39 | High-refractive-index material | 3.13 | 0.94 | 1.17 | 3.3 |
| 40 | Low-refractive-index material | 1.14 | 0.95 | 2.97 | 3.28 |
| 41 | High-refractive-index material | 2.83 | 1.16 | 1.65 | 3.3 |
| 42 | Low-refractive-index material | 1.67 | 0.59 | 3.02 | 3.28 |
| 43 | High-refractive-index material | 3.05 | 3.62 | 0.85 | 3.3 |
| 44 | Low-refractive-index material | 0.58 | 0.99 | — | 3.28 |
| 45 | High-refractive-index material | 3.71 | 3.16 | — | 3.3 |
| 46 | Low-refractive-index material | 1.54 | 1.16 | — | 3.28 |
| 47 | High-refractive-index material | — | 3.16 | — | 3.3 |
| 48 | Low-refractive-index material | — | 1.16 | — | 3.28 |
| 49 | High-refractive-index material | — | 3.16 | — | 2.81 |
| 50 | Low-refractive-index material | — | 1.16 | — | 2.13 |
| 51 | High-refractive-index material | — | 3.16 | — | 2.83 |
| 52 | Low-refractive-index material | — | 1.16 | — | 0.64 |
| 53 | High-refractive-index material | — | 3.16 | — | 3.44 |
| 54 | Low-refractive-index material | — | 1.16 | — | 1.61 |
| 55 | High-refractive-index material | — | 3.16 | — | — |
| 56 | Low-refractive-index material | — | 1.16 | — | — |
| 57 | High-refractive-index material | — | 3.16 | — | — |
| 58 | Low-refractive-index material | — | 1.16 | — | — |
| 59 | High-refractive-index material | — | 2.71 | — | — |
| 60 | Low-refractive-index material | — | 2.05 | — | — |
| 61 | High-refractive-index material | — | 2.75 | — | — |
| 62 | Low-refractive-index material | — | 1.55 | — | — |
| 63 | High-refractive-index material | — | 2.85 | — | — |
| 64 | Low-refractive index material | — | 1.91 | — | — |

\* The constitution of the film is shown in order from the side of the flat-plate-like transparent substrate 120.
\* The optical film thickness is shown in a multiple number of λ/4.

That is, the dichroic mirrors of a and b of Table 2 comprise: stacked layers that efficiently reflect light of λ and in which an average optical film thickness of a high-refractive-index material is approximately 3×λ/4 and that of a low-refractive-index material is approximately λ/4; and stacked layers that reflect the light on the short wavelength side from the light selected by the first wavelength selection member and in which the average optical film thickness of the high-refractive-index material is approximately λ/4, and that of the low-refractive-index material is approximately λ/4. A preferable range of the average optical film thickness in these examples depends on selected λ. In the stacked layer that efficiently reflects the central wavelength λ of the light selected by the first wavelength selection member, the average film thickness of the high-refractive-index material is preferably in a range of 2.9 to 3.4 times with respect to λ/4, and the average film thickness of the low-refractive-index material is preferably in a range of 0.9 to 1.2 times with respect to λ/4. In the stacked layer that reflects the light on the short wavelength side from the light selected by the first wavelength selection member, the average optical film thickness of the high-refractive-index material is preferably in a range of 0.8 to 1.1 times with respect to λ/4, and the average film thickness of the low-refractive-index material is preferably in a range of 0.8 to 1.1 times with respect to λ/4.

Additionally, spectral transmittance characteristics of the dichroic mirror coats of a in Table 2 are shown in FIG. 15, and those of the dichroic mirror coats of b in Table 2 are shown in FIG. 16. As apparent from FIGS. 15 and 16, even in either example, the central wavelength λ of the light selected by the first wavelength selection member is not transmitted in 0-degree incidence.

In another example supposed to be preferable, the dichroic mirror coat 124 corresponding to the present embodiment comprises: a stacked layer that efficiently reflects λ and in which an average optical film thickness of a high-refractive-index material is approximately λ/4 and that of a low-refractive-index material is approximately 3×λ/4 with respect to the central wavelength λ of the light selected by the first wavelength selection member; and a stacked layer that reflects the light on the short wavelength side from the light selected by the first wavelength selection member and in which the average optical film thickness of the high-refractive-index material is approximately λ/4 and that of the low-refractive-index material is approximately λ/4. In this case, the dichroic mirror coat 124 has a reflection band near the wavelength λ, a reflection band broadened on the short wavelength side, and a transmission band on the long wavelength side from the reflection band. Examples of the corresponding dichroic mirror coat 124 include a dichroic mirror coat having a film constitution in c of Table 2, In the film constitutions of the dichroic mirror coats of c of Table 2, 22 to 39 stacked layers efficiently reflect the central wavelength λ of the light selected by the first wavelength selection member. Assuming that λ is 490 nm, the average optical film thickness of the high-refractive-index material is approximately 1.17×λ/4, and that of the low-refractive-index material is approximately 3.21×λ/4. Moreover, four to 17 stacked layers reflect the light on the short wavelength side from the central wavelength λ of the light selected by the first wavelength selection member. Assuming that λ is 490 nm, the average optical film thickness of the high-refractive-index material is approximately 0.96×λ/4, and that of the low-refractive-index material is approximately 0.95×λ/4.

That is, the dichroic mirrors of c of Table 2 comprise: stacked layers that efficiently reflect light of λ and in which the average optical film thickness of the high-refractive-index material is approximately λ/4 and that of the low-refractive-index material is approximately 3×λ/4; and stacked layers that reflect the light on the short wavelength side from the light selected by the first wavelength selection member and in which the average optical film thickness of the high-refractive-index material is approximately λ/4, and that of the low-refractive-index material is approximately λ/4. A preferable range of the average optical film thickness in these examples depends on selected λ. In the stacked layer that efficiently reflects the central wavelength λ of the light selected by the first wavelength selection member, the average optical film thickness of the high-refractive-index material is preferably in a range of 0.9 to 1.2 times with respect to λ/4, and the average film thickness of the low-refractive-index material is preferably in a range of 2.9 to 3.4 times with respect to λ/4. In the stacked layer that reflects the light on the short wavelength side from the light selected by the first wavelength selection member, the average optical film thickness of the high-refractive-index material is preferably in a range of 0.8 to 1.1 times with respect to λ/4, and the average film thickness of the low-refractive-index material is preferably in a range of 0.8 to 1.1 times with respect to λ/4.

Additionally, spectral transmittance characteristics of the dichroic mirror coats of c of Table 2 are shown in FIG. 17. As apparent from FIG. 17, the central wavelength λ of the light selected by the first wavelength selection member is not transmitted in 0-degree incidence.

In still another example, the coat comprises: a stacked layer that efficiently reflects λ and in which an average optical film thickness of the high-refractive-index material is approximately 3×λ/4, and that of the low-refractive-index material is approximately 3×λ/4 with respect to the central wavelength λ of the light selected by the first wavelength selection member; and a stacked layer that reflects the light on the short wavelength side from the light selected by the first wavelength selection member and in which the average film thickness of the high-refractive-index material is approximately λ/4 and that of the low-refractive-index material is approximately λ/4. In this case, the dichroic mirror coat 124 has a reflection band near the wavelength λ, a reflection band broadened on the short wavelength side, and a transmission band on the long wavelength side from the reflection band. Examples of the corresponding dichroic mirror coat 124 include dichroic mirror coats having film constitution in d of Table 2. In the film constitutions of the dichroic mirror coats of d of Table 2, the stacked layers that efficiently reflect the central wavelength λ of the light selected by the first wavelength selection member correspond to 29 to 48 layers. Assuming that λ is 515 nm, the average optical film thickness of the high-refractive-index material is approximately 3.30×λ/4, and that of the low-refractive-index material is approximately 3.28×λ/4. The stacked layers that reflect the light on the short wavelength side from the central wavelength λ of the light selected by the first wavelength selection member correspond to 5 to 24 layers. Assuming that λ is 515 nm in the same manner as described above, the average optical film thickness of the high-refractive-index material is approximately 0.95×λ/4, and that of the low-refractive-index material is approximately 0.96×λ/4.

That is, the dichroic mirrors of d of Table 2 comprise: stacked layers that efficiently reflect light of λ and in which the average optical film thickness of the high-refractive-index material is approximately 3×λ/4 and that of the low-refractive-index material is approximately 3×λ/4; and stacked layers that reflect the light on the short wavelength side from the light selected by the first wavelength selection member and in which the average optical film thickness of the high-refractive-index material is approximately λ/4, and that of the low-refractive-index material is approximately λ/4. A preferable range of the average optical film thickness in these examples depends on selected λ. In the stacked layer that efficiently reflects the central wavelength λ of the light selected by the first wavelength selection member, the average optical film thickness of the high-refractive-index material is preferably in a range of 2.9 to 3.4 times with respect to λ/4, and the average film thickness of the low-refractive-index material is preferably in a range of 2.9 to 3.4 times with respect to λ/4. In the stacked layer that reflects the light on the short wavelength side from the light selected by the first wavelength selection member, the average optical film thickness of the high-refractive-index material is preferably in a range of 0.8 to 1.1 times with respect to λ/4, and the average film thickness of the low-refractive-index material is preferably in a range of 0.8 to 1.1 times with respect to λ/4.

Additionally, spectral transmittance characteristics of the dichroic mirror coats of d of Table 2 are shown in FIG. 18. As apparent from FIG. 18, the central wavelength λ of the light selected by the first wavelength selection member is not transmitted in 0-degree incidence.

According to the dichroic mirror coat 124 as in this example, separation of PS-polarization generated in a case where the light splitter is disposed at 45 degrees with respect to the optical axis can be reduced as compared with the above-described three examples (a, b, c of Table 2).

The light splitter 120 can secure the reflection band by a plurality of stacked layer portions of the dichroic mirror coat 124 disposed on the front surface of the flat-plate-like transparent substrate 122. Therefore, it is possible to broaden the reflection band of the light splitter 120. Accordingly, it is possible to apply a member having a transmittance characteristic that the transmission band is broad to the first wavelength selection member 110 (e.g., a case shown in FIG. 15). The light splitter 120 efficiently transmits the fluorescence generated from the sample 40, but most of quantity of exciting light transmitted through the light splitter 120 can be eliminated, and therefore the generation of the noise can be reduced by the above-described function. The present invention is also applicable to a case where a member having a transmittance characteristic of an ultra broad band is applied to the first wavelength selection member 110.

An optical element using color glass that satisfactorily absorbs the light having the wavelength selected by the first wavelength selection member in the substrate is applied to the second wavelength selection member 130 in many cases in order to reduce noises by obliquely incident light. However, in the present embodiment, since the light splitter 120 also satisfactorily interrupts the light generated by the scattering on the first wavelength selection member 110 and directed to the second wavelength selection member 130, the optical element using color glass that satisfactorily absorbs the obliquely incident light in the substrate does not have to be applied to the second wavelength selection member 130.

THIRD EMBODIMENT

A whole constitution of an epi-illumination microscope according to a third embodiment of the present invention is substantially the same as that of the first embodiment, and is therefore as shown in FIG. 1. However, in the present embodiment, spectral characteristics of a first dichroic mirror coat 124 and a second dichroic mirror coat 126 of a light splitter 120 are different from those of the first embodiment. In the present embodiment, the first dichroic mirror coat 124 and the second dichroic mirror coat 126 have spectral characteristics that substantially the same band is reflected, and substantially the same band is transmitted.

That is, the second dichroic mirror coat 126 reflects light of substantially the same wavelength band as that of a reflection band of the first dichroic mirror coat 124. Furthermore, the first dichroic mirror coat 124 and the second dichroic mirror coat 126 transmit fluorescence emitted from the sample.

In the light splitter 120 of the present embodiment, a transmittance of exciting light is lowered by square as compared with a conventional stacked layer in which a dichroic mirror coat is disposed only on one face thereof. As a result, the light splitter 120 of the present embodiment substantially completely reflects the exciting light, and suppresses transmission in a case where a first wavelength selection member 110 has a narrow band.

As a result, noise generation by irregular reflection on a fluorescence filter cassette side face wall can be suppressed.

The first dichroic mirror coat 124 is preferably formed by 20 or more stacked layers of a high-refractive-index material having a refractive index of 2.0 or more and a low-refractive-index material having a refractive index of 1.5 or less in the same manner as in the first embodiment. Details have been described in the first embodiment.

Furthermore, the second dichroic mirror coat 126 is preferably formed by 20 or more stacked layers of a high-refractive-index material having a refractive index of 2.0 or more and a low-refractive-index material having a refractive index of 1.5 or less. In one example, an average optical film thickness of the high-refractive-index material is approximately λ/4, and that of the low-refractive-index material is approximately λ/4. In this case, the second dichroic mirror coat 126 has a reflection band near a wavelength λ, and has a transmission band on a long wavelength side from the reflection band.

The second dichroic mirror coat 126 can satisfactorily complement the reflection band of the first dichroic mirror coat 124.

In the present embodiment, since the light splitter 120 also satisfactorily interrupts light generated by scattering on the first wavelength selection member 110 and directed toward a second wavelength selection member 130, an optical element using color glass satisfactorily absorbing obliquely incident light in a substrate does not have to be applied to the second wavelength selection member 130. As a result, efficient fluorescence observation can be performed with less noise. Furthermore, it is possible to apply an optical element using eco glass in a substrate to the second wavelength selection member 130. As a result, a glass member of a microscope may comprise only eco glass friendly to global environment.

Even in the present embodiment, as to film thicknesses of the first dichroic mirror coat 124 and the second dichroic mirror coat 126, a ratio of the film thickness (physical film thickness of the first dichroic mirror coat 124 divided by that of the second dichroic mirror coat 126) may be preferably larger than ⅓ and smaller than 3. Therefore, a stress by an interference film constituting the first dichroic mirror coat 124 and that by the interference film constituting the second dichroic mirror coat 126 are substantially offset. Therefore, generation of warpage of the flat-plate-like transparent substrate 122 that is a transparent member is inhibited. This enhances illumination and observation performances.

FOURTH EMBODIMENT

A whole constitution of an epi-illumination microscope according to a fourth embodiment of the present invention is substantially the same as that of the first embodiment, and is therefore as shown in FIG. 1. However, in the present embodiment, spectral characteristics of a first dichroic mirror coat 124 and a second dichroic mirror coat 126 of a light splitter 120 are different from those of the first embodiment.

FIG. 19 shows a transmittance characteristic Td2 of a first wavelength selection member 110, a transmittance characteristic Ta2 of the first dichroic mirror coat 124 disposed on the front surface of a flat-plate-like transparent substrate 122, and a transmittance characteristic Tb2 of the second dichroic mirror coat 126 disposed on the back surface of the flat-plate-like transparent substrate 122 in the fourth embodiment of the present invention.

As shown in FIG. 19, a transmission band of a short wavelength side of the transmittance characteristic Td2 of the first wavelength selection member 110 is positioned in a reflection band of the transmittance characteristic Ta2 of the first dichroic mirror coat 124. The reflection band of the transmittance characteristic Tb2 of the second dichroic mirror coat 126 is position on the long wavelength side from the reflection band of the transmittance characteristic Ta2 of the first dichroic mirror coat 124. The reflection band of the transmittance characteristic Ta2 of the first dichroic mirror coat 124 is not superimposed upon that of the transmittance characteristic Tb2 of the second dichroic mirror coat 126, and the bands are separated. In FIG. 19, Tf3 denotes the transmittance characteristic of the second wavelength selection member 130.

As seen from FIG. 19, the first dichroic mirror coat 124 reflects the exciting light transmitted through the first wavelength selection member 110. The second dichroic mirror coat 126 reflects the light on the long wavelength side with respect to the reflection band of the first dichroic mirror coat 124. Furthermore, the first dichroic mirror coat 124 and the second dichroic mirror coat 126 transmit fluorescence emitted from a sample.

In the present embodiment, the light splitter 120 has a reflection band on the long wavelength side in addition to the wavelength band of the exciting light. Therefore, self fluorescence of a certain band generated by the first wavelength selection member 110 can be cut. As a result, for example, when the first wavelength selection member 110 is largely influenced by red self fluorescence, a dichroic mirror coat reflecting red wavelength light is applied to the second dichroic mirror coat 126. For example, in a case where sensitivity of near-infrared band of a TV camera, and self fluorescence of the near-infrared band is cut, a dichroic mirror coat reflecting the near-infrared band is applied to the second dichroic mirror coat 126, and accordingly noises can be reduced.

The first dichroic mirror coat 124 is preferably formed by 20 or more stacked layers of a high-refractive-index material having a refractive index of 2.0 or more and a low-refractive-index material having a refractive index of 1.5 or less in the same manner as in the first embodiment. Details have been described in the first embodiment.

In the present embodiment, since the light splitter 120 also satisfactorily interrupts light generated by scattering on the first wavelength selection member 110 and directed toward a second wavelength selection member 130, an optical element using color glass satisfactorily absorbing obliquely incident light in a substrate does not have to be applied to the second wavelength selection member 130. As a result, efficient fluorescence observation can be performed with less noise. Furthermore, it is possible to apply an optical element using eco glass in a substrate to the second wavelength selection member 130. As a result, a glass member of a microscope may comprise only eco glass friendly to global environment.

Even in the present embodiment, as to film thicknesses of the first dichroic mirror coat 124 and the second dichroic mirror coat 126, a ratio of the film thickness (physical film thickness of the first dichroic mirror coat 124 divided by that of the second dichroic mirror coat 126) may be preferably larger than 1/3 and smaller than 3. Therefore, a stress by an interference film constituting the first dichroic mirror coat 124 and that by the interference film constituting the second dichroic mirror coat 126 are substantially offset. Therefore, generation of warpage of the flat-plate-like transparent substrate 122 that is a transparent member is inhibited. This enhances illumination and observation performances.

FIFTH EMBODIMENT

A whole constitution of an epi-illumination microscope according to a fifth embodiment of the present invention is substantially the same as that of the first embodiment, and is therefore as shown in FIG. 1. However, in the present embodiment, spectral characteristics of a first dichroic mirror coat 124 and a second dichroic mirror coat 126 of a light splitter 120 are different from those of the first embodiment. In the present embodiment, there are two wavelengths of light selected by a first wavelength selection member 110 and a second wavelength selection member 130, and the light splitter 120 is also accordingly coated.

FIG. 20 shows a transmittance characteristic Td3 of the first wavelength selection member 110, a transmittance characteristic Ta3 of the first dichroic mirror coat 124 disposed on the front surface of a flat-plate-like transparent substrate 122, a transmittance characteristic Tb3 of the second dichroic mirror coat 126 disposed on the back surface of the flat-plate-like transparent substrate 122, and a transmittance characteristic Tf3 of the second wavelength selection member 130.

As shown in FIG. 20, the transmittance characteristic Td3 of the first wavelength selection member 110 has two transmission bands. The transmission band on a short wavelength side of the transmittance characteristic Td3 of the first wavelength selection member 110 is positioned in a reflection band of the transmittance characteristic Ta3 of the first dichroic mirror coat 124. The reflection band of the transmittance characteristic Tb3 of the second dichroic mirror coat 126 is positioned on the long wavelength side from the reflection band of the transmittance characteristic Ta3 of the first dichroic mirror coat 124. The reflection band of the transmittance characteristic Ta3 of the first dichroic mirror coat 124 is not superimposed on that of the transmittance characteristic Tb3 of the second dichroic mirror coat 126, and the bands are separated. The transmission band on the long wavelength side of the transmittance characteristic Td3 of the first wavelength selection member 110 is positioned in the reflection band of the transmittance characteristic Tb3 of the second dichroic mirror coat 126.

As seen from FIG. 20, the first dichroic mirror coat 124 reflects exciting light on the short wavelength side transmitted through the first wavelength selection member 110. The second dichroic mirror coat 126 reflects the exciting light on the long wavelength side transmitted through the first wavelength selection member 110. The first dichroic mirror coat 124 and the second dichroic mirror coat 126 transmit fluorescence having two wavelengths emitted from a sample irradiated with the exciting light having two wavelengths transmitted through the first wavelength selection member 110. Furthermore, the second wavelength selection member 130 selectively transmits only fluorescence having two wavelengths emitted from a sample irradiated with the exciting light having two wavelengths, and forms an image in a predetermined position of the detection device 60 to form a fluorescent image on a sample 40.

As a result, it is possible to simultaneously observe the fluorescence having two wavelengths.

In a conventional two-wavelength excitation fluorescence filter set, a dichroic mirror coat having two reflection bands is disposed on the front surface of the light splitter. The dichroic mirror coat has a low reflectance as compared with a dichroic mirror coat having only one reflection band.

Therefore, in two-wavelength excitation, noises are easily generated as compared with one-wavelength excitation.

In the present embodiment, each of the first dichroic mirror coat 124 and the second dichroic mirror coat 126 has only one reflection band. Therefore, the light splitter 120 of the present embodiment corresponds to two-wavelength excitation without involving drop of the reflectance. As a result, generation of noises is inhibited.

In the present embodiment, an example in which two wavelengths are selected has been described, but the fluorescence having three or more wavelengths can be simultaneously observed.

The first dichroic mirror coat 124 is preferably formed by 20 or more stacked layers of a high-refractive-index material having a refractive index of 2.0 or more and a low-refractive-index material having a refractive index of 1.5 or less in the same manner as in the first embodiment. Details have been described in the first embodiment.

In the present embodiment, since the light splitter 120 also satisfactorily interrupts light generated by scattering on the first wavelength selection member 110 and directed toward a second wavelength selection member 130, an optical element using color glass satisfactorily absorbing obliquely incident light in a substrate does not have to be applied to the second wavelength selection member 130. As a result, efficient fluorescence observation can be performed with less noise. Furthermore, it is possible to apply an optical element using eco glass in a substrate to the second wavelength selection member 130. As a result, a glass member of a microscope may comprise only eco glass friendly to global environment.

Even in the present embodiment, as to film thicknesses of the first dichroic mirror coat 124 and the second dichroic mirror coat 126, a ratio of the film thickness (physical film thickness of the first dichroic mirror coat 124 divided by that of the second dichroic mirror coat 126) may be preferably larger than ⅓ and smaller than 3. Therefore, a stress by an interference film constituting the first dichroic mirror coat 124 and that by the interference film constituting the second dichroic mirror coat 126 are substantially offset. Therefore, generation of warpage of the flat-plate-like transparent substrate 122 that is a transparent member is inhibited. This enhances illumination and observation performances.

The embodiments of the present invention have been described above with reference to the drawings, but the present invention is not limited to these embodiments, and various modifications or alterations may be performed without departing from the scope of the present invention.

The epi-illumination microscope of each embodiment of the present invention described above is based on an upright microscope, but technical concepts of the present invention for use in each embodiment can be simply applied to an inverted microscope.

Moreover, as a light source, one or a plurality of monochromatic light sources may be used such as laser light sources. In this case, since an excitation wavelength is selected on a light source side, a first wavelength selection member is not required.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. An epi-illumination microscope comprising:
   a light source that emits light to illuminate a sample;
   a first wavelength selection member that selectively transmits the light from the light source;
   a light splitter that reflects the light from the first wavelength selection member to epi-illuminate the sample and transmits the light emitted from the sample, the light splitter comprising a transparent member and a dichroic mirror coat disposed on the transparent member, the transparent member including a first surface and a second surface, the dichroic mirror coat comprising a first dichroic mirror coat disposed on the first surface of the transparent member and having a first transmittance characteristic, and a second dichroic mirror coat disposed on the second surface of the transparent member and having a second transmittance characteristic, a reflection band of the second transmittance characteristic of the second dichroic mirror is shifted from and partially overlaps with a reflection band of the first transmittance characteristic; and
   a second wavelength selection member that selectively transmits the light transmitted through the light splitter.

2. The epi-illumination microscope according to claim 1, wherein the first dichroic mirror coat is formed by stacking 20 or more layers of high-refractive-index materials having a refractive index of 2.0 or more and low-refractive-index material having a refractive index of 1.5 or less, an average optical film thickness of the high-refractive-index material is approximately $3\times\lambda/4$, and that of the low-refractive-index material is approximately $\lambda/4$ with respect to a central wavelength $\lambda$ of the light selected by the first wavelength selection member, and the first dichroic mirror coat has a reflection band that reflects the light from the first wavelength selection member near the wavelength $\lambda$, and a transmission band that transmits the light emitted from the sample on a long wavelength side from the reflection band.

3. The epi-illumination microscope according to claim 1, wherein the first dichroic mirror coat is formed by stacking 20 or more layers of high-refractive-index materials having a refractive index of 2.0 or more and low-refractive-index material having a refractive index of 1.5 or less, an average optical film thickness of the high-refractive-index material is approximately $\lambda/4$, and that of the low-refractive-index material is approximately $3\times\lambda/4$ with respect to a central wavelength $\lambda$ of the light selected by the first wavelength selection member, and the first dichroic mirror coat has a reflection band that reflects the light from the first wavelength selection member near the wavelength $\lambda$, and a transmission band that transmits the light emitted from the sample on a long wavelength side from the reflection band.

4. The epi-illumination microscope according to claim 1, wherein the first dichroic mirror coat is formed by stacking 20 or more layers of high-refractive-index materials having a refractive index of 2.0 or more and low-refractive-index material having a refractive index of 1.5 or less, an average optical film thickness of the high-refractive-index material is approximately $3\times\lambda/4$, and that of the low-refractive-index material is approximately $3\times\lambda/4$ with respect to a central wavelength $\lambda$ of the light selected by the first wavelength selection member, and the first dichroic mirror coat has a reflection band that reflects the light from the first wavelength selection member near the wavelength $\lambda$, and a transmission band that transmits the light emitted from the sample on a long wavelength side from the reflection band.

5. The epi-illumination microscope according to claim 1, wherein the second dichroic mirror coat is formed by stacking 20 or more layers of high-refractive-index materials having a refractive index of 2.0 or more and low-refractive-index material having a refractive index of 1.5 or less, an average optical film thickness of the high-refractive-index material is approximately $\lambda/4$, and that of the low-refractive-index material is approximately $\lambda/4$ with respect to light $\lambda$ on the short wavelength side, light $\lambda$ on the long wavelength side, light $\lambda$ of the same band, or a central wavelength $\lambda$ of combined light, and the second dichroic mirror coat has a reflection band near the wavelength $\lambda$, and a transmission band on the long wavelength side from the reflection band.

6. The epi-illumination microscope according to claim 5, wherein the first dichroic mirror coat is formed by stacking 20 or more layers of high-refractive-index materials having a refractive index of 2.0 or more and low-refractive-index material having a refractive index of 1.5 or less, an average optical film thickness of the high-refractive-index material is approximately $3\times\lambda/4$, and that of the low-refractive-index material is approximately $\lambda/4$ with respect to a central wavelength $\lambda$ of the light selected by the first wavelength selection member, and the first dichroic mirror coat has a reflection band near the wavelength $\lambda$, and a transmission band on the long wavelength side from the reflection band.

7. The epi-illumination microscope according to claim 5, wherein the first dichroic mirror coat is formed by stacking 20 or more layers of high-refractive-index materials having a refractive index of 2.0 or more and low-refractive-index material having a refractive index of 1.5 or less, an average optical film thickness of the high-refractive-index material is approximately $\lambda/4$, and that of the low-refractive-index material is approximately $3\times\lambda/4$ with respect to a central wavelength $\lambda$ of the light selected by the first wavelength selection member, and the first dichroic mirror coat has a reflection band near the wavelength $\lambda$, and a transmission band on the long wavelength side from the reflection band.

8. The epi-illumination microscope according to claim 5, wherein the first dichroic mirror coat is formed by stacking 20 or more layers of high-refractive-index materials having a refractive index of 2.0 or more and low-refractive-index material having a refractive index of 1.5 or less, an average optical film thickness of the high-refractive-index material is approximately $3\times\lambda/4$, and that of the low-refractive-index material is approximately $3\times\lambda/4$ with respect to a central wavelength $\lambda$ of the light selected by the first wavelength selection member, and the first dichroic mirror coat has a reflection band near the wavelength $\lambda$, and a transmission band on the long wavelength side from the reflection band.

9. The epi-illumination microscope according to claim 1, wherein the first wavelength selection member selectively transmits light having a plurality of wavelengths within the light from the light source, the light splitter reflects the light transmitted through the first wavelength selection member, and transmits the light having a plurality of wavelengths emitted from the sample, and the second wavelength selection member selectively transmits light having a plurality of predetermined wavelengths within the light transmitted through the light splitter.

10. The epi-illumination microscope according to claim 9, wherein the first dichroic mirror coat reflects light having at least one wavelength within the light having the plurality of wavelengths selected by the first wavelength selection member to epi-illuminate the sample.

11. The epi-illumination microscope according to claim 10, wherein the second dichroic mirror coat reflects light having a wavelength that is not reflected by the first dichroic mirror coat within the light having the plurality of wavelengths selected by the first wavelength selection member to epi-illuminate the sample.

12. The epi-illumination microscope according to claim 1, wherein a ratio of a film thickness of the first dichroic mirror coat to that of the second dichroic mirror coat (physical film thickness of the first dichroic mirror coat divided by that of the second dichroic mirror coat) is larger than $\frac{1}{3}$ and smaller than 3.

13. The epi-illumination microscope according to claim 1, wherein the reflection band of the second transmittance characteristic is positioned on a short wavelength side from the reflection band of the first transmittance characteristic.

14. The epi-illumination microscope according to claim 1, wherein the reflection band of the second transmittance characteristic is positioned on a long wavelength side from the reflection band of the first transmittance characteristic.

15. A fluorescence filter set comprising:
a first wavelength selection member that selectively transmits exciting light;
a light splitter that reflects the exciting light from the first wavelength selection member to epi-illuminate a sample and transmits fluorescence emitted from the sample, the light splitter comprising a transparent member and a dichroic mirror coat disposed on the transparent member, the transparent member including a first surface and a second surface, the dichroic mirror coat comprising a first dichroic mirror coat disposed on the first surface of the transparent member and having a first transmittance characteristic, and a second dichroic mirror coat disposed on the second surface of the transparent member and having a second transmittance characteristic, a reflection band of the second transmittance characteristic of the second dichroic mirror is shifted from and partially overlaps with a reflection band of the first transmittance characteristic; and
a second wavelength selection member that selectively transmits the fluorescence transmitted through the light splitter.

16. The fluorescence filter set according to claim 15, wherein the first dichroic mirror coat is formed by stacking 20 or more layers of high-refractive-index materials having a refractive index of 2.0 or more and low-refractive-index material having a refractive index of 1.5 or less, an average optical film thickness of the high-refractive-index material is approximately $3\times\lambda/4$, and that of the low-refractive-index material is approximately $\lambda/4$ with respect to a central wavelength $\lambda$ of the light selected by the first wavelength selection member, and the first dichroic mirror coat has a reflection band that reflects the light from the first wavelength selection member near the wavelength $\lambda$, and a transmission band that transmits the light emitted from the sample on a long wavelength side from the reflection band.

17. The fluorescence filter set according to claim 15, wherein the first dichroic mirror coat is formed by stacking 20 or more layers of high-refractive-index materials having a refractive index of 2.0 or more and low-refractive-index material having a refractive index of 1.5 or less, an average optical film thickness of the high-refractive-index material is approximately $\lambda/4$, and that of the low-refractive-index material is approximately $3\times\lambda/4$ with respect to a central wavelength $\lambda$ of the light selected by the first wavelength selection member, and the first dichroic mirror coat has a reflection band that reflects the light from the first wavelength selection member near the wavelength $\lambda$, and a transmission band that transmits the light emitted from the sample on a long wavelength side from the reflection band.

18. The fluorescence filter set according to claim 15, wherein the first dichroic mirror coat is formed by stacking 20 or more layers of high-refractive-index materials having a refractive index of 2.0 or more and low-refractive-index material having a refractive index of 1.5 or less, an average optical film thickness of the high-refractive-index material is approximately $3\times\lambda/4$, and that of the low-refractive-index material is approximately $3\times\lambda/4$ with respect to a central wavelength $\lambda$ of the light selected by the first wavelength selection member, and the first dichroic mirror coat has a reflection band that reflects the light from the first wavelength selection member near the wavelength $\lambda$, and a transmission band that transmits the light emitted from the sample on a long wavelength side from the reflection band.

19. The fluorescence filter set according to claim 15, wherein the second dichroic mirror coat is formed by stacking 20 or more layers of high-refractive-index materials having a refractive index of 2.0 or more and low-refractive-index material having a refractive index of 1.5 or less, an average optical film thickness of the high-refractive-index material is approximately $\lambda/4$, and that of the low-refractive-index material is approximately $\lambda/4$ with respect to light $\lambda$ on the short wavelength side, light $\lambda$ on the long wavelength side, light $\lambda$ of the same band, or a central wavelength $\lambda$ of combined light, and the second dichroic mirror coat has a reflection band near the wavelength $\lambda$, and a transmission band on the long wavelength side from the reflection band.

20. The fluorescence filter set according to claim 19, wherein the first dichroic mirror coat is formed by stacking 20 or more layers of high-refractive-index materials having a refractive index of 2.0 or more and low-refractive-index material having a refractive index of 1.5 or less, an average optical film thickness of the high-refractive-index material is approximately $3\times\lambda/4$, and that of the low-refractive-index material is approximately $\lambda/4$ with respect to a central wavelength $\lambda$ of the light selected by the first wavelength selection member, and the first dichroic mirror coat has a reflection band near the wavelength $\lambda$, and a transmission band on the long wavelength side from the reflection band.

21. The fluorescence filter set according to claim 19, wherein the first dichroic mirror coat is formed by stacking 20 or more layers of high-refractive-index materials having a refractive index of 2.0 or more and low-refractive-index material having a refractive index of 1.5 or less, an average optical film thickness of the high-refractive-index material is approximately $\lambda/4$, and that of the low-refractive-index material is approximately $3\times\lambda/4$ with respect to a central wavelength $\lambda$ of the light selected by the first wavelength selection member, and the first dichroic mirror coat has a reflection band near the wavelength $\lambda$, and a transmission band on the long wavelength side from the reflection band.

22. The fluorescence filter set according to claim 19, wherein the first dichroic mirror coat is formed by stacking 20 or more layers of high-refractive-index materials having a refractive index of 2.0 or more and low-refractive-index material having a refractive index of 1.5 or less, an average optical film thickness of the high-refractive-index material is approximately $3\times\lambda/4$, and that of the low-refractive-index material is approximately $3\times\lambda/4$ with respect to a central wavelength $\lambda$ of the light selected by the first wavelength selection member, and the first dichroic mirror coat has a reflection band near the wavelength $\lambda$, and a transmission band on the long wavelength side from the reflection band.

23. The fluorescence filter set according to claim 15, wherein the first wavelength selection member selectively transmits light having a plurality of wavelengths within the light from the light source, the light splitter reflects the light transmitted through the first wavelength selection member, and transmits the light having a plurality of wavelengths emitted from the sample, and the second wavelength selection member selectively transmits light having a plurality of predetermined wavelengths within the light transmitted through the light splitter.

24. The fluorescence filter set according to claim 23, wherein the first dichroic mirror coat reflects light having at least one wavelength within the light having the plurality of wavelengths selected by the first wavelength selection member to epi-illuminate the sample.

25. The fluorescence filter set according to claim 24, wherein the second dichroic mirror coat reflects light having a wavelength that is not reflected by the first dichroic mirror coat within the light having the plurality of wavelengths selected by the first wavelength selection member to epi-illuminate the sample.

26. The fluorescence filter set according to claim 15, wherein a ratio of a film thickness of the first dichroic mirror coat to that of the second dichroic mirror coat (physical film thickness of the first dichroic mirror coat divided by that of the second dichroic mirror coat) is larger than $\frac{1}{3}$ and smaller than 3.

27. The fluorescence filter set according to claim 15, wherein the reflection band of the second transmittance characteristic is positioned on a short wavelength side from the reflection band of the first transmittance characteristic.

28. The fluorescence filter set according to claim 15, wherein the reflection band of the second transmittance characteristic is positioned on a long wavelength side from the reflection band of the first transmittance characteristic.

* * * * *